US012663425B2

(12) United States Patent
Bartolini et al.

(10) Patent No.: US 12,663,425 B2
(45) **Date of Patent: *Jun. 23, 2026**

(54) DELTA-2-TUBULIN AS A BIOMARKER AND THERAPEUTIC TARGET FOR PERIPHERAL NEUROPATHY

(71) Applicants: THE TRUSTEES OF COLUMBIA UNIVERSITY IN THE CITY OF NEW YORK, New York, NY (US); UNIVERSITÀ DEGLI STUDI DI MILANO-BICOCCA, Milan (IT)

(72) Inventors: Francesca Bartolini, New York, NY (US); Maria Elena Pero, New York, NY (US); Guido Cavaletti, Monza (IT)

(73) Assignees: The Trustees of Columbia University in The City of New York, New York, NY (US); Università Degli Studi Di Milano-Bicocca, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/529,720

(22) Filed: Dec. 5, 2023

(65) Prior Publication Data

US 2024/0110931 A1 Apr. 4, 2024

Related U.S. Application Data

(60) Division of application No. 16/884,768, filed on May 27, 2020, now Pat. No. 11,874,284, which is a continuation of application No. PCT/US2018/063129, filed on Nov. 29, 2018.

(60) Provisional application No. 62/650,133, filed on Mar. 29, 2018, provisional application No. 62/592,247, filed on Nov. 29, 2017.

(51) Int. Cl.
| | |
|---|---|
| *G01N 33/68* | (2006.01) |
| *A61K 31/69* | (2006.01) |
| *A61K 31/7105* | (2006.01) |
| *A61K 45/06* | (2006.01) |
| *A61P 25/02* | (2006.01) |
| *G01N 33/575* | (2026.01) |

(52) U.S. Cl.
CPC ......... *G01N 33/6896* (2013.01); *A61K 31/69* (2013.01); *A61K 31/7105* (2013.01); *A61K 45/06* (2013.01); *A61P 25/02* (2018.01); *G01N 33/575* (2026.01); *G01N 2800/2842* (2013.01); *G01N 2800/52* (2013.01)

(58) Field of Classification Search
CPC ....... G01N 33/6896; G01N 2800/2842; G01N 33/574; G01N 2800/52; G01N 33/575; A61K 31/69; A61K 31/7105; A61K 45/06; A61K 31/337; A61K 33/243; A61P 25/02; C12Q 2600/118; C12Q 2600/158; C12Q 1/6883
See application file for complete search history.

(56) References Cited

U.S. PATENT DOCUMENTS

| | | | |
|---|---|---|---|
| 6,506,559 B1 | 1/2003 | Fire et al. | |
| 6,573,099 B2 | 6/2003 | Graham | |
| 7,410,659 B2 | 8/2008 | Rosenbloom | |
| 11,874,284 B2 * | 1/2024 | Bartolini ............. | C12Q 1/6883 |
| 2008/0026401 A1 | 1/2008 | Feder et al. | |
| 2010/0303785 A1 | 12/2010 | Gozes et al. | |

FOREIGN PATENT DOCUMENTS

| | | |
|---|---|---|
| WO | WO 1999/032619 A1 | 7/1999 |
| WO | WO 2001/036646 A1 | 5/2001 |
| WO | WO 2001/068836 A2 | 9/2001 |
| WO | WO 2016/169698 A1 | 10/2016 |

OTHER PUBLICATIONS

U.S. Appl. No. 16/884,768 (U.S. Appl. No. 11,874,284), filed May 27, 2020 (Jan. 16, 2024).
U.S. Appl. No. 16/884,768, Dec. 5, 2023 Issue Fee Payment.
U.S. Appl. No. 16/884,768, Sep. 7, 2023 Notice of Allowance.
U.S. Appl. No. 16/884,768, Jul. 7, 2023 Amendment and Request for Continued Examination (RCE).
U.S. Appl. No. 16/884,768, Feb. 10, 2023 Notice of Appeal Filed.
U.S. Appl. No. 16/884,768, Aug. 10, 2022 Final Office Action.
U.S. Appl. No. 16/884,768, Jul. 26, 2022 Response to Non-Final Office Action.
U.S. Appl. No. 16/884,768, Feb. 4, 2022 Non-Final Office Action.
U.S. Appl. No. 16/884,768, Dec. 9, 2021 Amendment and Request for Continued Examination (RCE).
U.S. Appl. No. 16/884,768, Oct. 7, 2021 Final Office Action.
U.S. Appl. No. 16/884,768, Sep. 27, 2021 Response to Non-Final Office Action.
U.S. Appl. No. 16/884,768, May 27, 2021 Non-Final Office Action.
U.S. Appl. No. 16/884,768, Apr. 5, 2021 Response to Restriction Requirement.
U.S. Appl. No. 16/884,768, Jan. 29, 2021 Restriction Requirement.
U.S. Appl. No. 16/884,768, Dec. 21, 2020 Response to Restriction Requirement.
U.S. Appl. No. 16/884,768, Oct. 27, 2020 Restriction Requirement.
Brummelkamp et al., "A System for Stable Expression of Short Interfering RNAs in Mammalina Cells," Science 296, 550-553 (2002).
Cavaletti et al., "Chemotherapy-induced peripheral neurotoxicity," Nature Reviews Neurology 6:657-666 (2010).

(Continued)

*Primary Examiner* — Olga N Chernyshev
(74) *Attorney, Agent, or Firm* — Baker Botts L.L.P.

(57) ABSTRACT

The present disclosure relates to delta-2-tubulin and its use as a biomarker for determining if a subject is at risk of developing peripheral neuropathy or if a subject has developed peripheral neuropathy. The present disclosure further relates to methods for the treatment of peripheral neuropathy in a subject and assays for identifying compounds that can be used to treat and/or prevent peripheral neuropathy.

9 Claims, 17 Drawing Sheets

(56)          References Cited

OTHER PUBLICATIONS

Figure 1A:
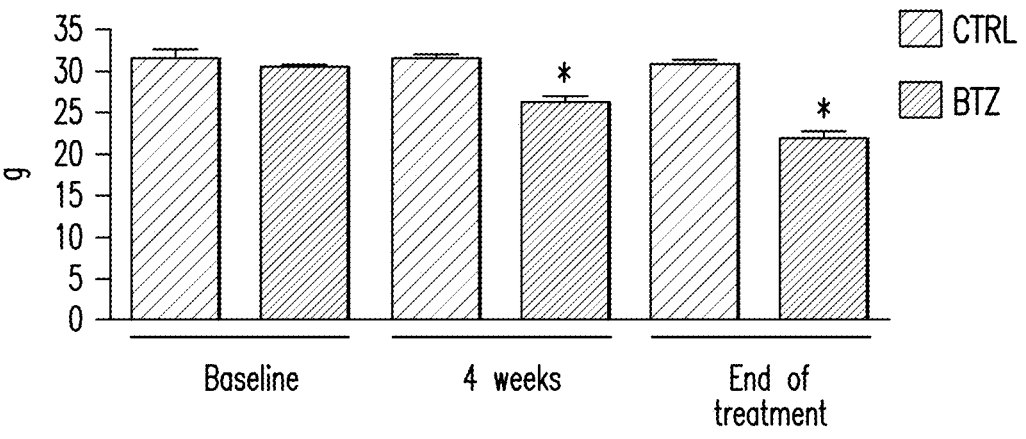
Figure 1B:
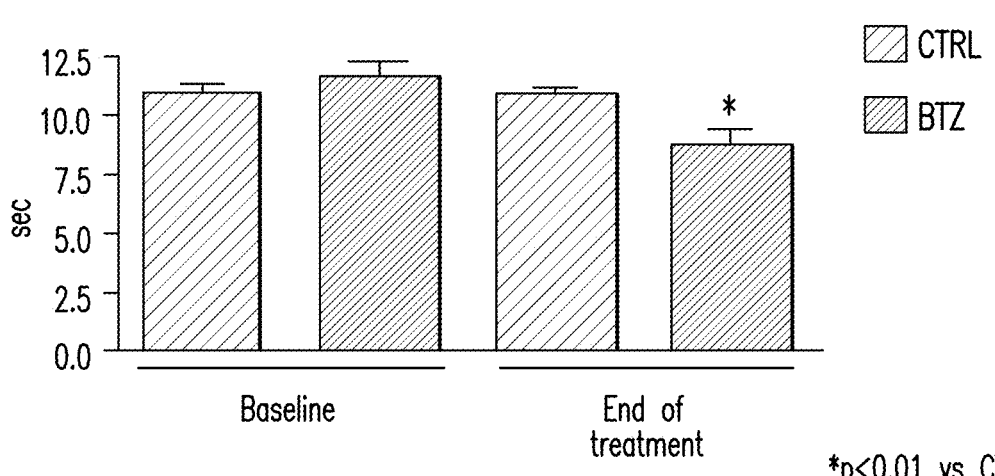
Figures 1C, 1D:
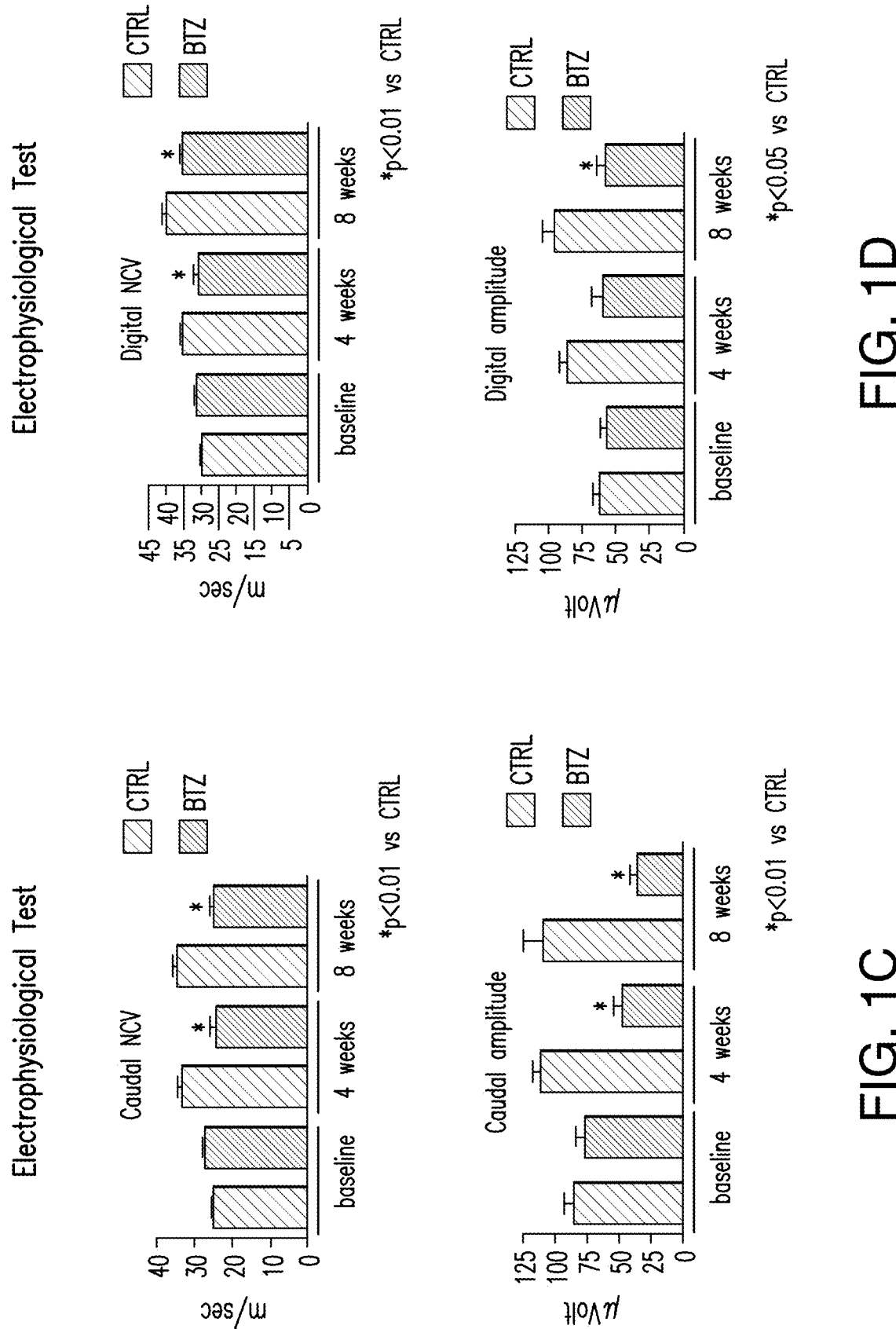

Elbashir et al., "Duplexes of 21-nucleotide RNAs mediate RNA interference in cultured mammalian cells," Nature 411, 494-497 (2001).

Ghosh-Roy et al., "kinesin-13 and tubulin post-translational modifications regulate microtubule growth in axon regeneration," Developmental Cell 23:716-728 (2012).

Hannon, "RNA interference," Nature 418:244-251 (2002).

Hong et al, "The influence of chemotherapy-induced neurotoxicity on psychological distress and sleep disturbance in cancer patients,". Curr. Oncol. 21(4):174-180 (2014).

International Search Report mailed Feb. 21, 2019 in International Application No. PCT/US2018/063129.

Janke et al., "Tubulin post-translational modifications: encoding functions on the neuronal microtubule cytoskeleton," Trends Neurosci, 33:362-372 (2010).

McManus et al., "Gene Silencing in Mammals by Small Interfering RNAs," Nature Reviews 3:737-747 (2002).

Rogowski et al., "A Family of Protein-Deglutamylating Enzymes Associated with Neurodegeneration," Cell 143:564-578 (2010).

Song et al., "Post-translational Modifications of Tubulin: Pathways to Functional Diversity of Microtubules," Trends Cell Biol. 25(3):125-136 (2015).

Soucek et al., "Normal and Prostate Cancer Cells Display Distinct Molecular Profiles of α-Tubulin Posttranslational Modifications," Prostate 66:954-965 (2006).

Tacchetti et al., "Bortezomib- and thalidomide-induced peripheral neuropathy in multiple myeloma: clinical and molecular analyses of a phase 3 study," Am J Hematol, 89:1085-1091 (2014).

Tuschl, et al., "Targeted mRNA degradation by double-stranded RNA in vitro," Genes Y Development 13:3191-3197 (1999).

UniProtKB Q9UPW5 (CBPC1_Human) (2007).

* cited by examiner

Dynamic Test

*p<0.01 vs CTRL

Plantar Test

*p<0.01 vs CTRL

Chronic treatment

FIG. 2

βIII- tubulin          D2- Tubulin

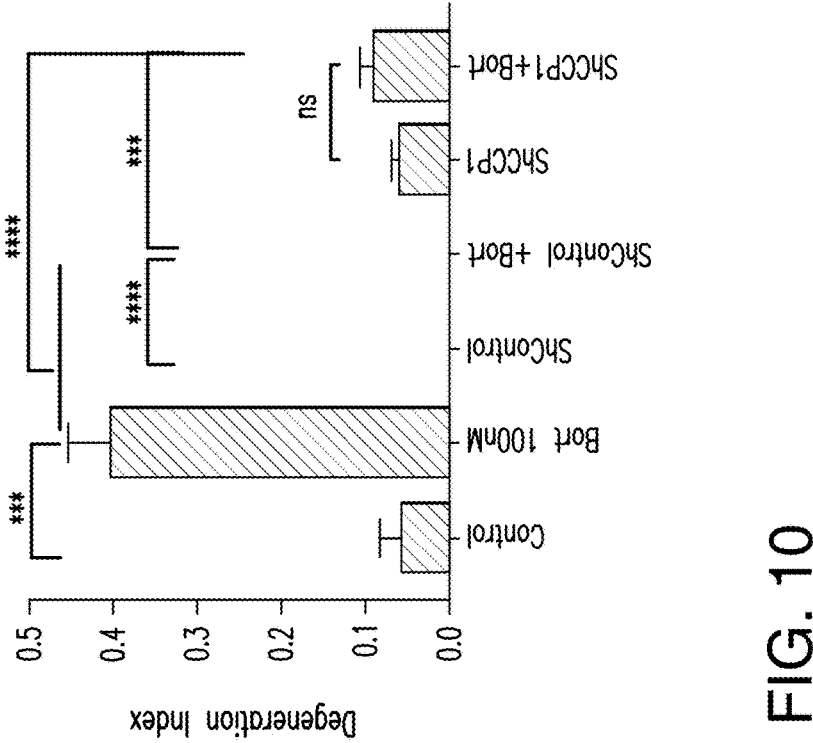
FIG. 10
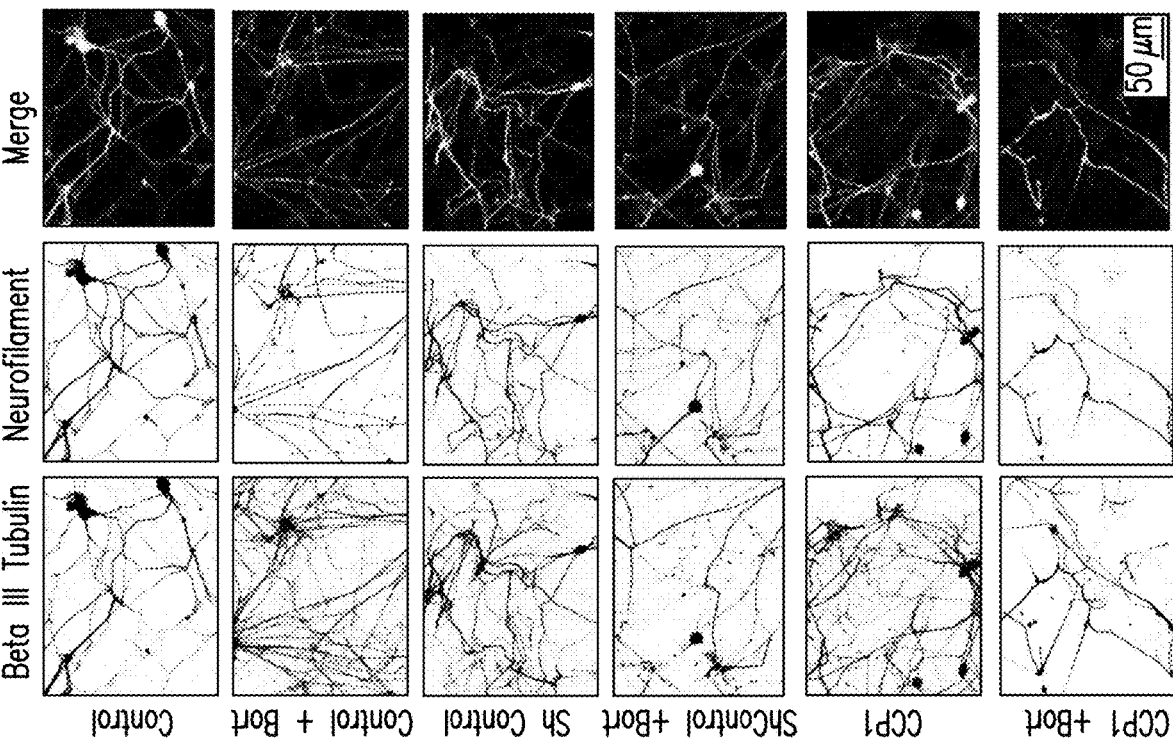

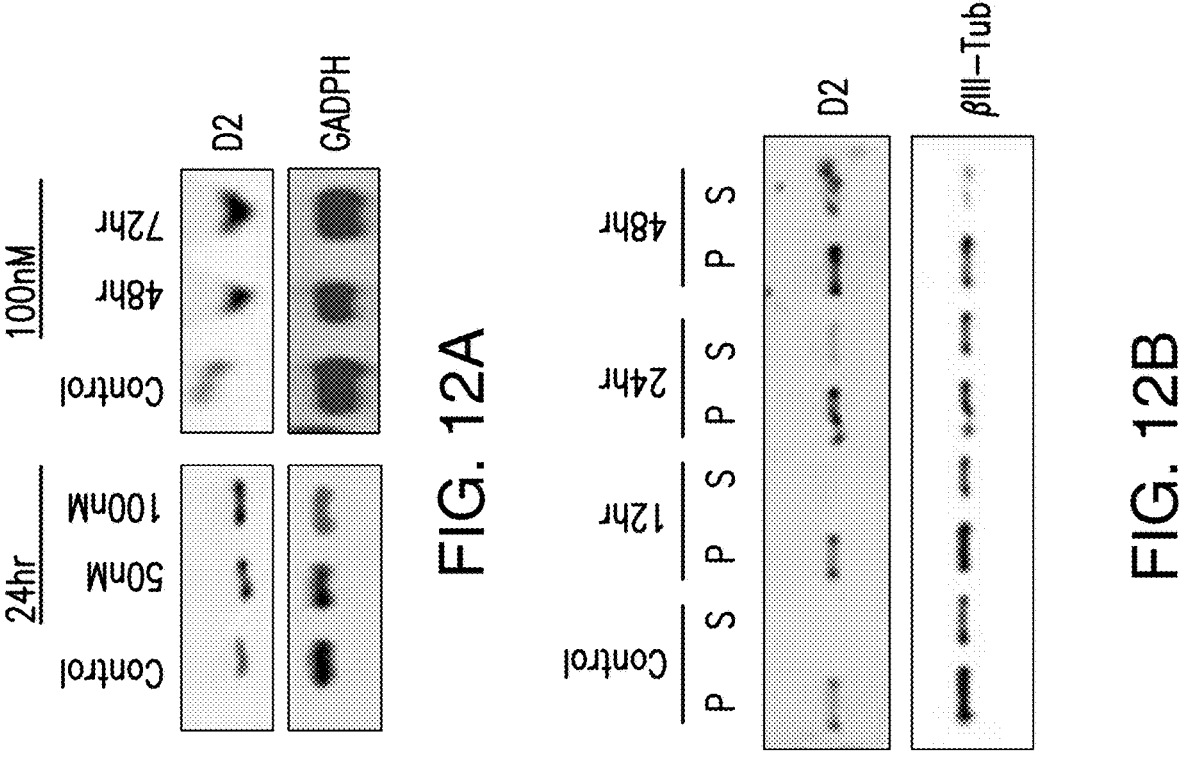
FIG. 12A
FIG. 12B
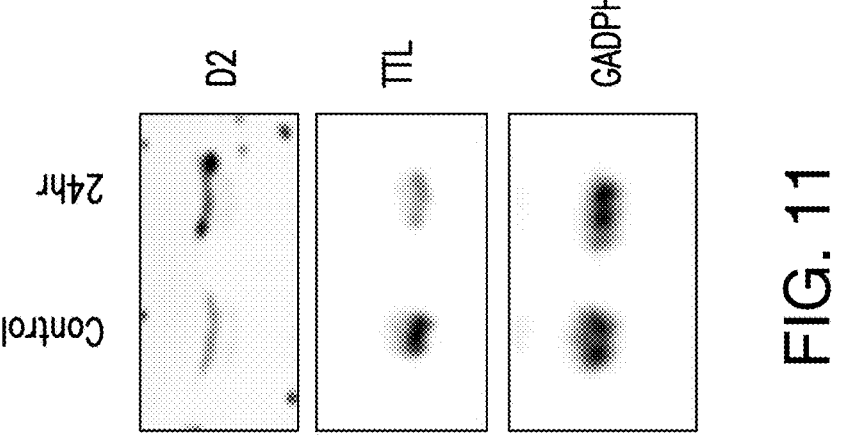
FIG. 11

Peripherin                    D2                    Merge

FIG. 13A

NF200                    D2                    Merge

FIG. 13B

TrkC                    D2                    Merge

FIG. 13C

TrkA                    D2                    Merge

FIG. 13D

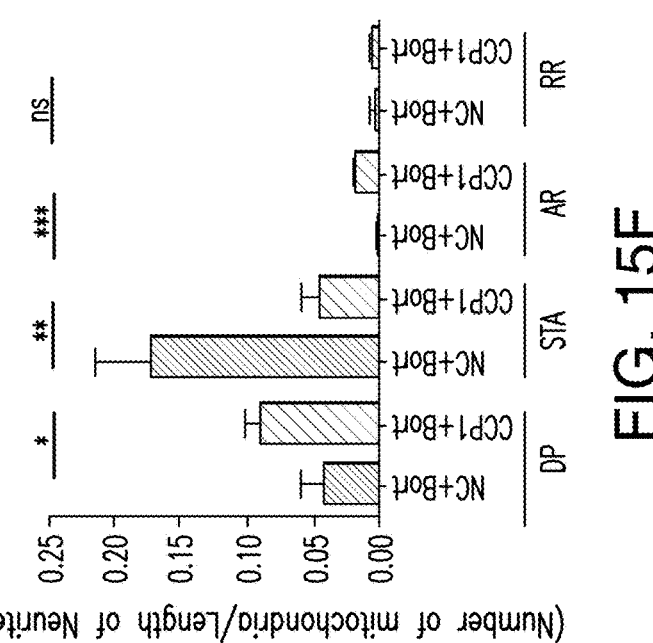
FIG. 15F
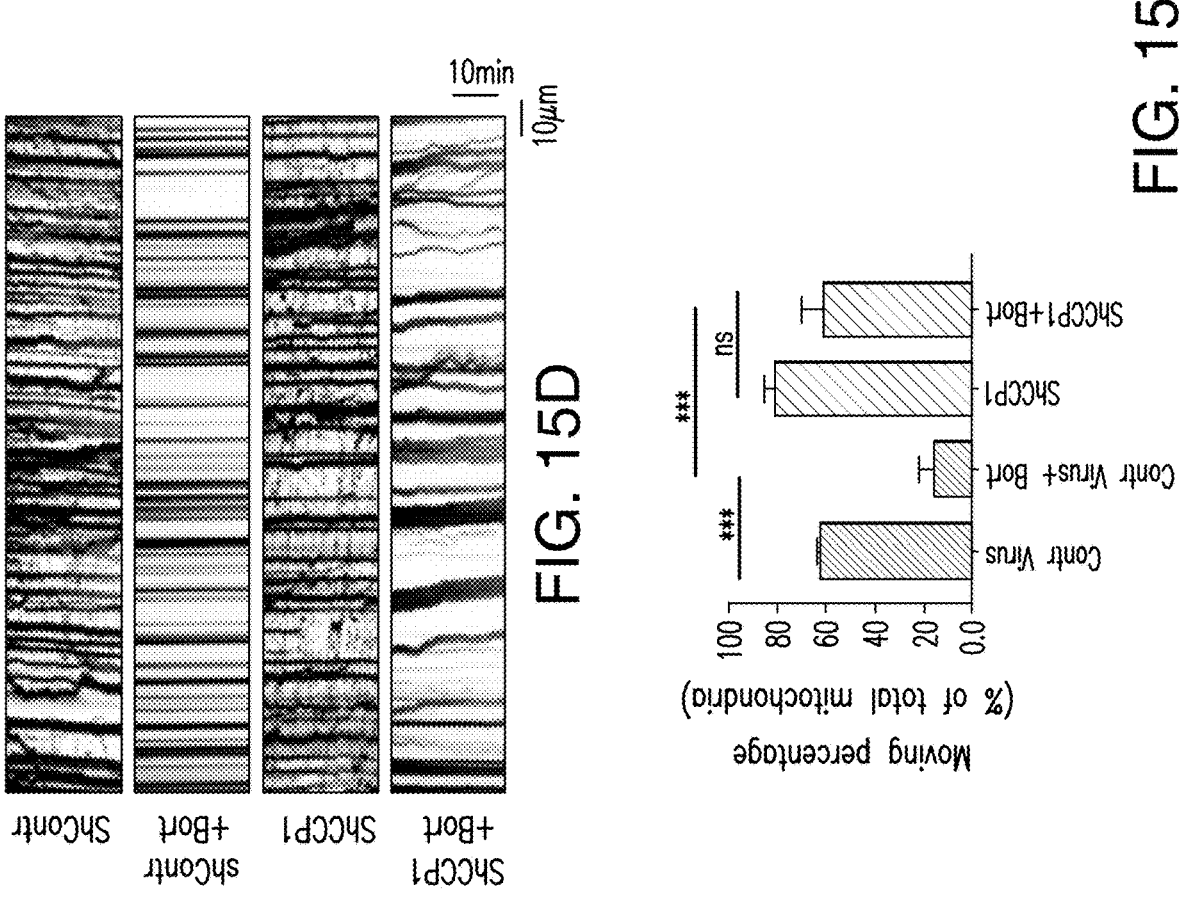
FIG. 15E
FIG. 15D

DELTA-2-TUBULIN AS A BIOMARKER AND THERAPEUTIC TARGET FOR PERIPHERAL NEUROPATHY

CROSS-REFERENCE TO RELATED APPLICATIONS

This application is a Divisional Application of U.S. patent application Ser. No. 16/884,768, filed May 27, 2020, which is a Continuation Application of International Patent Application No. PCT/US2018/063129, which claims priority to United States Provisional Application Ser. No. 62/592,247, filed Nov. 29, 2017, and U.S. Provisional Application Ser. No. 62/650,133, filed Mar. 29, 2018, to each of which priority is claimed and the contents of each of which are incorporated herein in their entireties.

1. INTRODUCTION

The present disclosure relates to delta-2-tubulin and its use as a biomarker for determining if a subject is at risk of developing peripheral neuropathy or if a subject has developed peripheral neuropathy. The present disclosure further relates to methods for the treatment of peripheral neuropathy in a subject and assays for identifying compounds that can be used to treat and/or prevent peripheral neuropathy.

2. BACKGROUND

Chemotherapy-induced peripheral neuropathy (CIPN) is a common adverse side effect of many chemotherapeutic agents. Symptoms can be typically sensory, or a combination of sensory and motor, and can include sensory discomfort, pain, numbness and tingling in the hands and feet and/or motor weakness, cranial nerve deficits or autonomic neuropathy (Hong et al. Curr. Oncol. 21(4):174-180 (2014)). CIPN can be acute or persistent and can result in compromised daily functioning and quality of life (Hong et al. (2014)).

CIPN is associated with the treatment of chemotherapeutic agents such as bortezomib, platinum-containing compounds and paclitaxel and is often the dose-limiting side effect of these agents (Cavaletti and Marmiroli, Nature Reviews Neurology 6:657-666 (2010)). CIPN can represent an important cause of discomfort and suffering in patients undergoing chemotherapy and can persist after termination of treatment with the chemotherapeutic agent. The incidence of CIPN is variable and can depend on many factors, including dose, cumulative dose, duration of treatment, combination therapy with other chemotherapeutic agents, as well as age and the presence of a high-risk pre-existing condition.

A challenge in managing and preventing CIPN has been that the pathogenesis of CIPN is not necessarily well understood, which can lead to a lack of an effective strategy for preventing or treating CIPN (Cavaletti and Marmiroli (2010)). Modification of the chemotherapy treatment of a patient can be required to limit the severity of CIPN, which can prevent patients from receiving effective cancer treatment (Cavaletti and Marmiroli (2010)). Therefore, there remains a need for effective methods for the treatment and prevention of CIPN and its symptoms.

Delta-2-tubulin (also referred to as "D2-tubulin") is a form of tubulin that has been post-translationally modified to lack the terminal tyrosine and penultimate glutamate residues (Janke and Kneussel, Trends in Neuroscience 33:362-

372 (2010)). Delta-2-tubulin is found in microtubules in neurons (Soucek et al., Prostate 66:954-955 (2006)).

3. SUMMARY

The present disclosure relates to delta-2-tubulin, its use as a biomarker of peripheral neuropathy, methods for the treatment of peripheral neuropathy in a subject and assays for identifying compounds that can be used to treat and/or prevent peripheral neuropathy. The disclosed subject matter recognizes that delta-2-tublin expression is increased in the cell bodies of peripheral neuronal cells upon treatment with chemotherapeutic compounds that result in chemotherapy-induced peripheral neuropathy.

The present disclosure provides methods for determining the risk of a subject of developing peripheral neuropathy. In certain embodiments, an example method can include (1) obtaining a sample from the subject prior to treatment of the subject with an anti-cancer agent, (2) treating the sample with the anti-cancer agent and (3) determining, in the treated sample, the expression level of a delta-2-tubulin biomarker, where if the expression level of the delta-2-tubulin biomarker is increased following treatment with the anti-cancer agent, then the subject is at an increased risk of developing peripheral neuropathy upon treatment with the anti-cancer agent. Alternatively, the method can include determining, in the treated sample, the expression level of a delta-2-tubulin biomarker, where if the expression level of the delta-2-tubulin biomarker is not increased following treatment with the anti-cancer agent, then the subject is at a reduced risk of developing peripheral neuropathy upon treatment with the anti-cancer agent.

The present disclosure further provides methods for determining whether a subject has developed peripheral neuropathy. In certain embodiments, an example method can include obtaining a sample from the subject after treatment with an anti-cancer agent, and determining, in the sample, the expression level of a delta-2-tubulin biomarker, where if the expression level of the delta-2-tubulin biomarker is increased following treatment with the anti-cancer agent as compared to a reference sample, then the subject has developed chemotherapy-induced peripheral neuropathy.

The present disclosure provides assays for identifying a compound for treatment of peripheral neuropathy. In certain embodiments, an example assay can include (1) contacting a sample with an anti-cancer agent that has been shown to induce peripheral neuropathy, (2) detecting the expression level of delta-2-tubulin to confirm the induction of peripheral neuropathy, (3) treating the sample with a drug candidate and (4) detecting the expression of delta-2-tubulin in the sample after treatment with the drug candidate, where if the expression level of delta-2-tubulin decreases after treatment with the drug candidate, then the drug candidate is an effective compound for treating peripheral neuropathy in a subject.

In certain embodiments, an assay for identifying an anti-cancer agent that has a reduced risk of inducing peripheral neuropathy can include contacting a sample with a drug candidate, and detecting the expression level of delta-2-tubulin, where if the drug candidate does not increase the expression level of delta-2-tubulin as compared to a reference sample, then the drug candidate has a reduced risk of inducing chemotherapy-induced peripheral neuropathy in a subject that will be treated with the drug candidate.

The present disclosure provides methods for treating peripheral neuropathy. In certain embodiments, an example method for treating peripheral neuropathy in a subject includes obtaining a sample from the subject after treatment with an anti-cancer agent, and determining, in the sample, the expression level of a delta-2-tubulin biomarker, where if the expression level of the delta-2-tubulin biomarker is increased following treatment with the anti-cancer agent as compared to a reference sample, then initiating treatment of the subject with a delta-2-tubulin inhibitor or a compound that inhibits delta-2-tubulin formation.

In certain embodiments, the methods of the present disclosure can include using immunofluorescence to determine the expression level of the delta-2-tubulin biomarker. In certain embodiments, Western Blot can be used to determine the expression level of the delta-2-tubulin biomarker. In certain embodiments, the sample can include one or more peripheral neuronal cells. In certain embodiments, the sample is a biopsy of a sural nerve from the subject. In certain embodiments, the sample is a dermal biopsy from the subject.

In certain embodiments, the anti-cancer agent is selected from the group consisting of oxaliplatin, cisplatin, carboplatin, paclitaxel, eribulin, thalidomide, a taxane, a vinca alkaloid and bortezomib. For example, but not by way of limitation, the anti-cancer agent is bortezomib.

The present disclosure further provides pharmaceutical compositions that include a delta-2-tubulin inhibitor or a compound that inhibits delta-2-tubulin formation and a pharmaceutically acceptable carrier. In certain embodiments, the compound that inhibits delta-2-tubulin formation is an inhibitor or an antagonist of CCP1, CCP4 or CCP6. In certain embodiments, the compound that inhibits delta-2-tubulin formation is an inhibitor or an antagonist of CCP1. In certain embodiments, the compound is an activator of TTL.

The present disclosure further provides kits for determining and/or evaluating the localization and/or expression level of a delta-2-tubulin biomarker in a sample of a subject, e.g., for determining if the subject is likely to have or develop neuropathy, e.g., CIPN. In certain embodiments, the kit provides for detecting the delta-2-tubulin biomarker in the subject and instructions, where the instructions state that a higher expression level of delta-2-tubulin in the sample following treatment with an anti-cancer agent, as compared to a reference control, is indicative that the subject will likely have neuropathy. In certain embodiments, the provision for detecting the delta-2-tubulin biomarker in the subject comprises one or more antibodies that specifically bind to the delta-2-tubulin biomarker.

4. BRIEF DESCRIPTION OF THE DRAWINGS

FIG. 1A-1D. Chronic doses of bortezomib affect animal behavior and nerve function. (A) Hind-paw withdrawal response to mechanical stimulus (10-50 g). (B) Plantar withdrawal latency response to heat source (infra-red light). Dynamic and plantar tests were performed before (baseline value), after 4-week and at the end point of treatment with Bortezomib. Data are expressed as mean values±SD, n animals=12. (C, D) Caudal and digital nerve conduction velocity (NCV) and amplitude measured in rats treated chronically with Bortezomib. n=8-10 per group; *p<0.05 compared to control.

Figure 2:
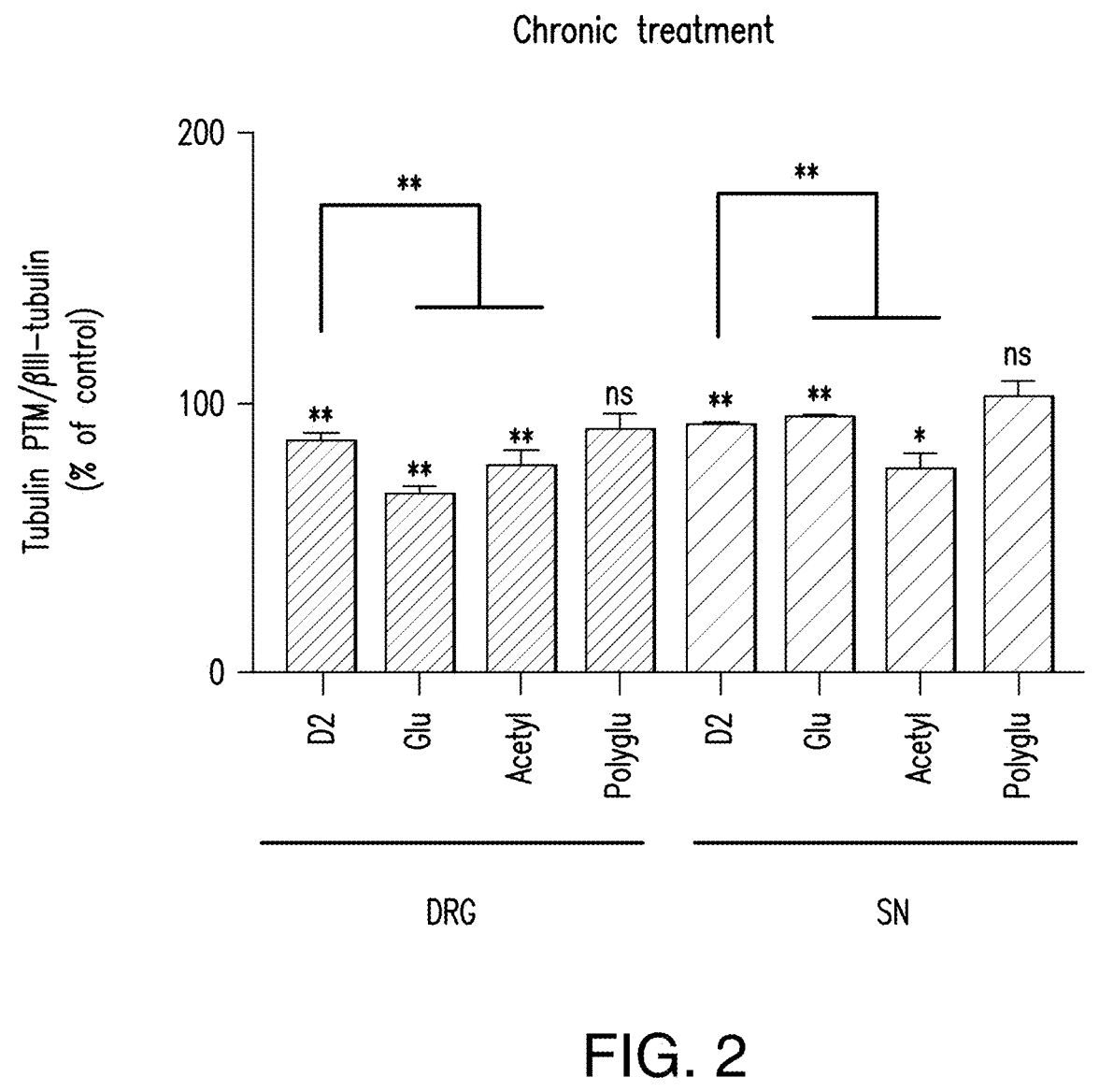

FIG. 2. Immunofluorescence analysis of selected α-tubulin post-translational modifications in neuronal tissue from chronically treated rats. Relative tubulin post-translational modifications levels measured by quantitative immunofluorescence in randomly selected dorsal root ganglion cell bodies (DRG) and sural nerve (SN) from rats (4 per group)

treated with chronic (0.2 mg/kg, 3× week for 8 weeks) doses of Bortezomib. Data are mean values±SEM. **, p≤0.0001; *, p≤0.001; **, p≤0.01; *, p≤0.05 by ANOVA (in red,) or unpaired, two-tailed t-test (in black).

Figures 3A, 3B, 3C:
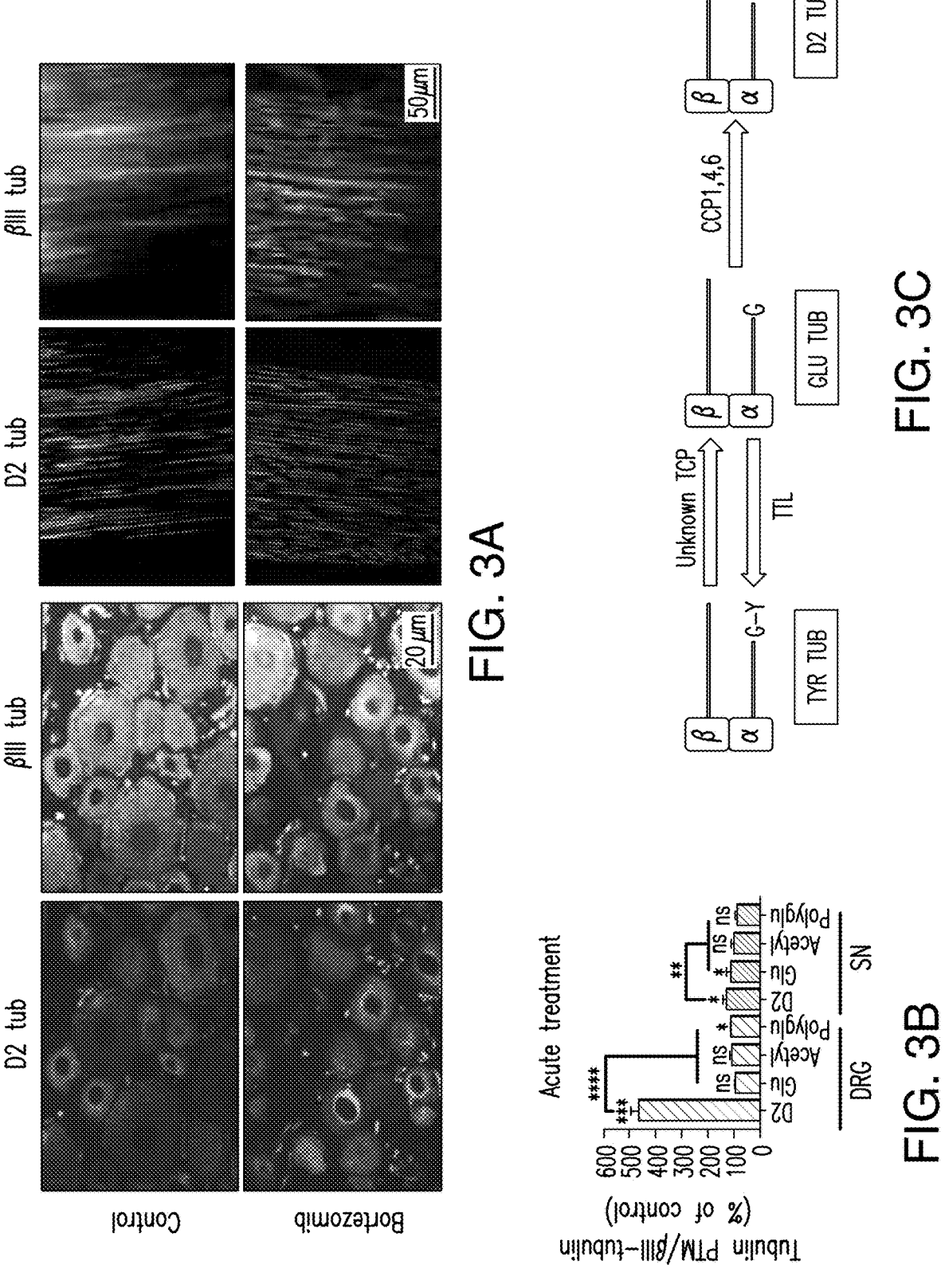

FIG. 3A-3C. Bortezomib acutely increases delta-2-tubulin in dorsal root ganglion (DRG) cell bodies in vivo. (A) Representative immunofluorescence staining of DRG isolated from rats acutely treated with Bortezomib. (B) Relative tubulin post-translational modifications levels measured by quantitative immunofluorescence in randomly selected DRG and SN from rats (4 per group) treated with acute (i.v. 0.2 mg/kg; 24 hr) doses of Bortezomib. Data are mean values±SEM, **, p≤0.0001; *, p≤0.001; **, p≤0.01; *, p≤0.05 by ANOVA (A in red,) or unpaired, two-tailed t-test (A in black). (C) Schematic of the enzymes involved in D2 generation.

Figure 4:
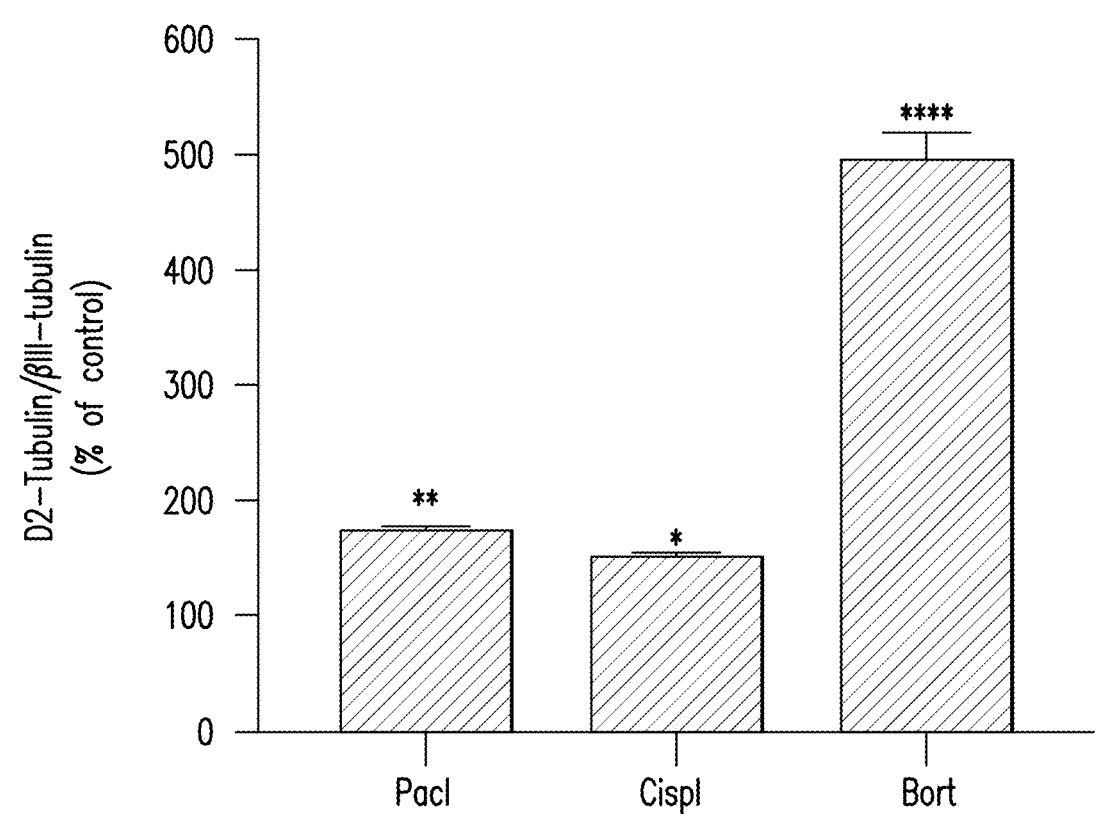

FIG. 4. Unrelated chemotherapy-induced peripheral neuropathy (CIPN) drugs acutely accumulate delta-2-tubulin in DRG neurons.

Figure 5A:
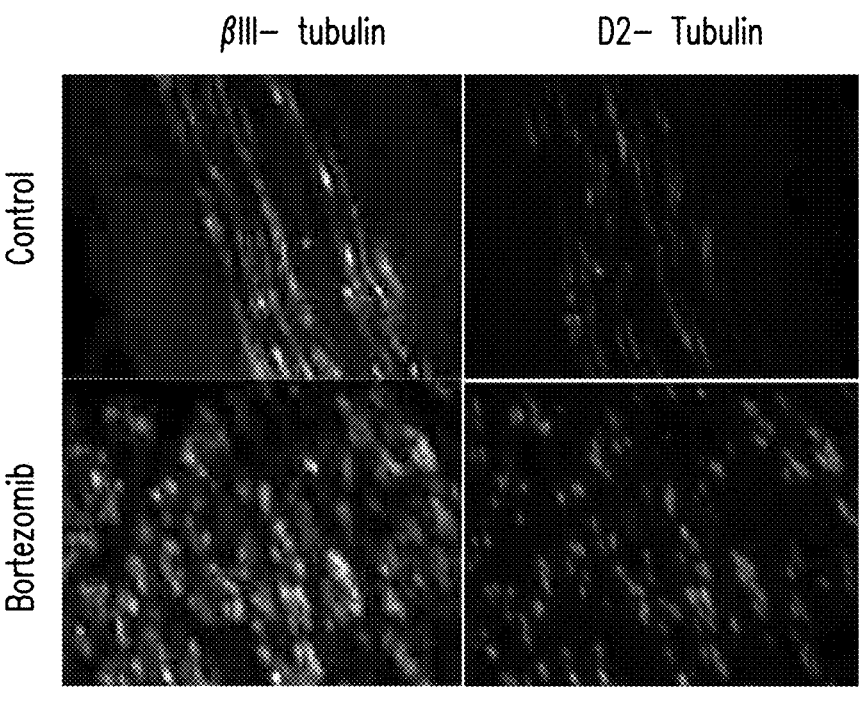
Figure 5B:
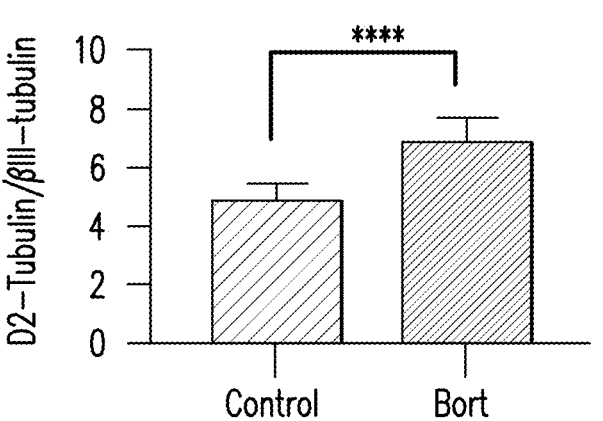
Figure 5C:
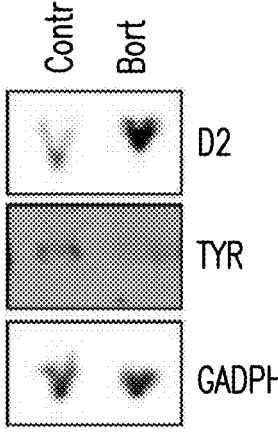

FIG. 5A-5C. Bortezomib induces delta-2-tubulin in CIPN patients. (A) Representative immunofluorescence staining of SN isolated from a patient affected by CIPN. (B) Ratio analysis of D2/βIII-tubulin levels measured by immunofluorescence of fixed tissue from one SN biopsy. Data are mean values from 3 sections±SEM, ****, p<0.0001 by t-test (unpaired, two-tailed). (C) Immunoblot of D2 levels in whole cell lysates from one SN biopsy. Tyr, tyrosinated tubulin.

Figure 6:
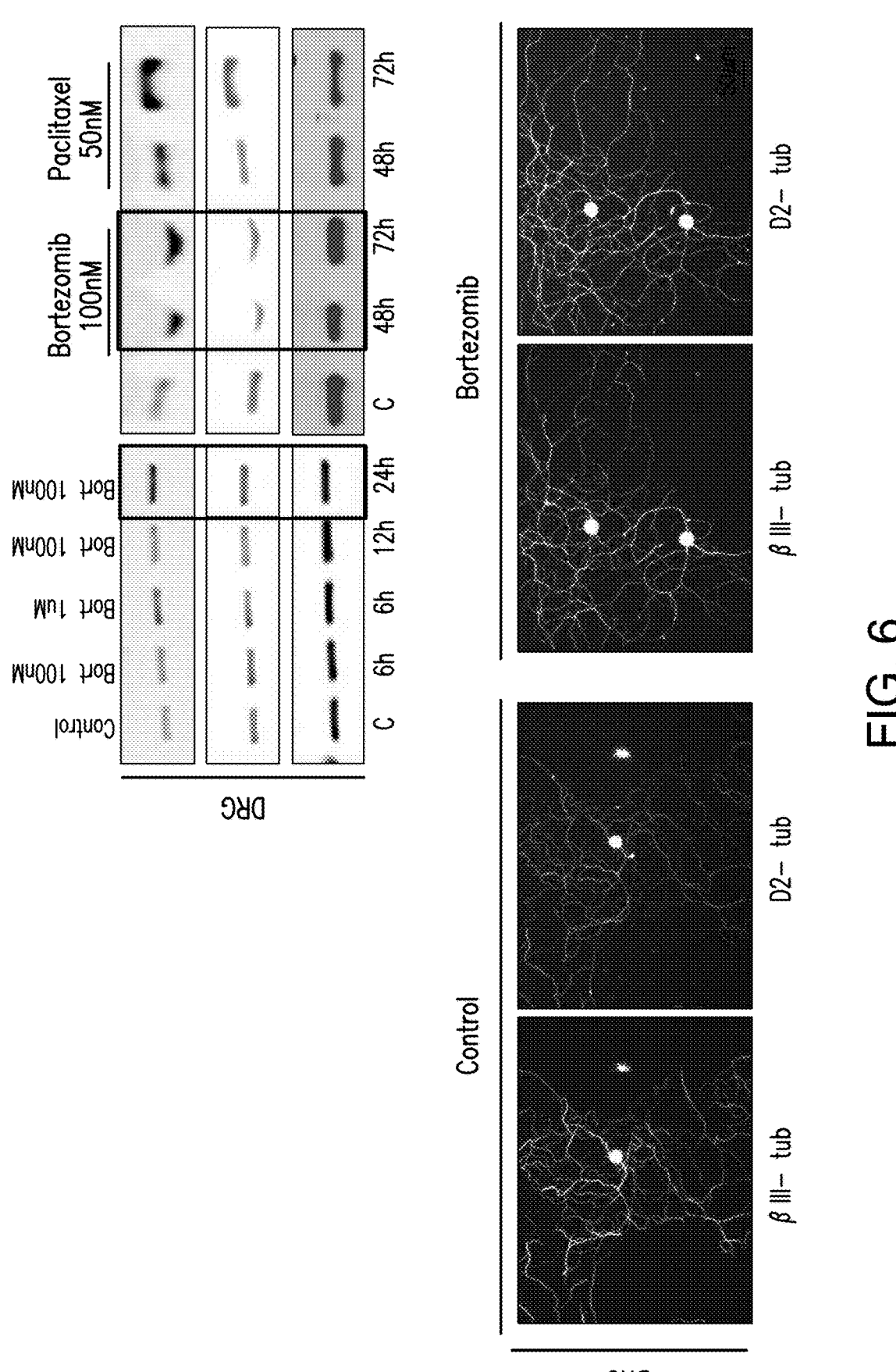
Figures 7A, 7B, 7C, 7D:
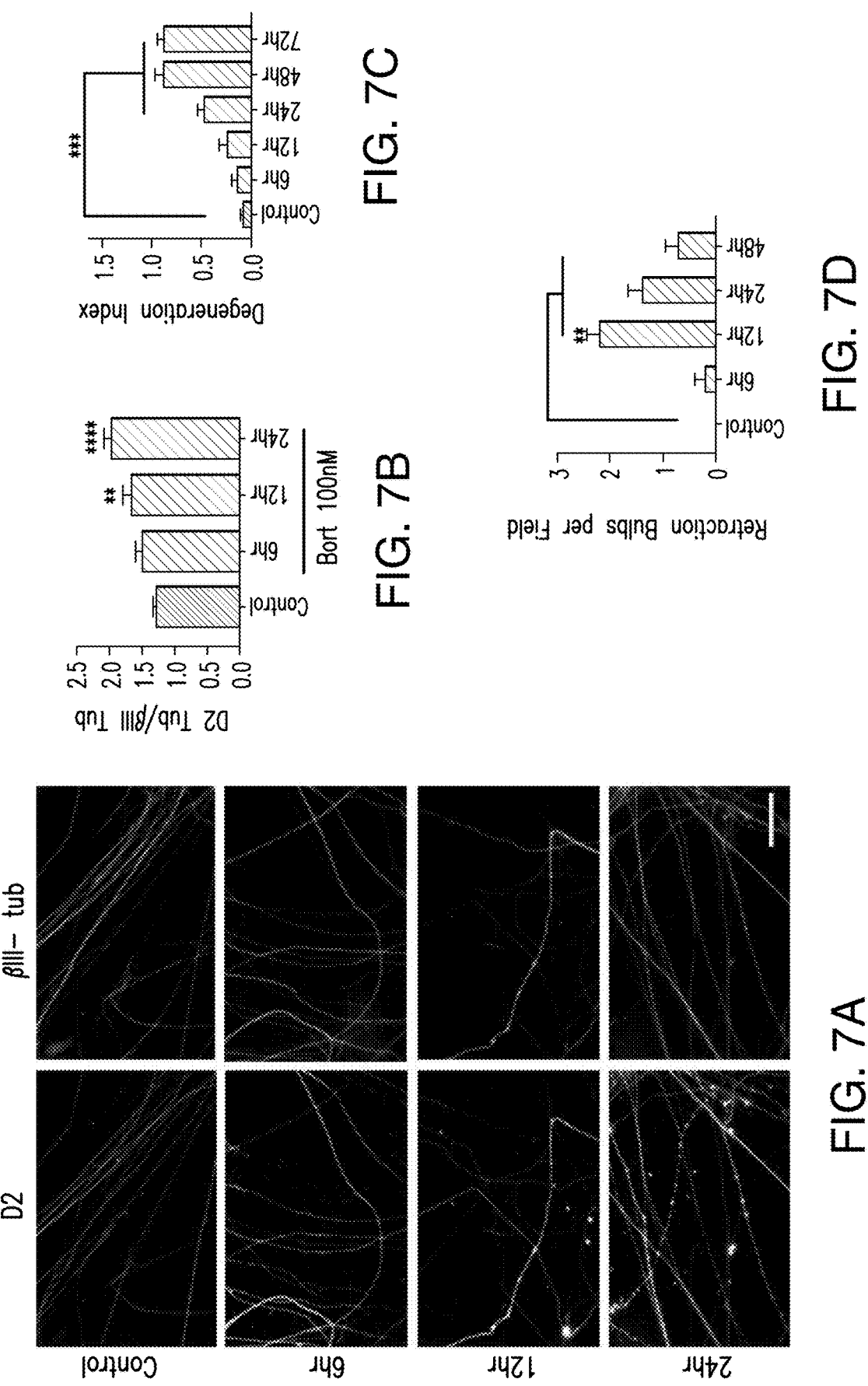

FIG. 6. Bortezomib induces delta-2-tubulin in DRG neurons as shown by western blot analysis of delta-2-tubulin levels from whole cell lysates of adult DRG neurons treated with Bortezomib and immunofluorescence of delta-2-tubulin in cultured DRG neurons treated with Bortezomib.

FIG. 7A-7D. Bortezomib induces delta-2-tubulin at the onset of axonal degeneration. (A) Representative immunofluorescence of D2 and βIII-tub staining in DRG neurons treated with 100 nM of Bortezomib for the indicated times. Bar, 50 μm. (B) Ratio analysis of D2/βIII-tubulin levels measured by immunofluorescence of fixed cells treated as in A. , p≤0.01, , p≤0.0001 by t-test (unpaired, two-tailed). (C) Time dependent increase of axonopathy in DRG neurons treated with 100 nM of Bortezomib for the indicated times. *, p<0.001 ANOVA. Data are mean values±SEM from 3 experiments. (D) Number of retraction bulbs per field in DRG neurons treated with 100 nM of Bortezomib for the indicated times. **, p≤0.01.

Figure 8:
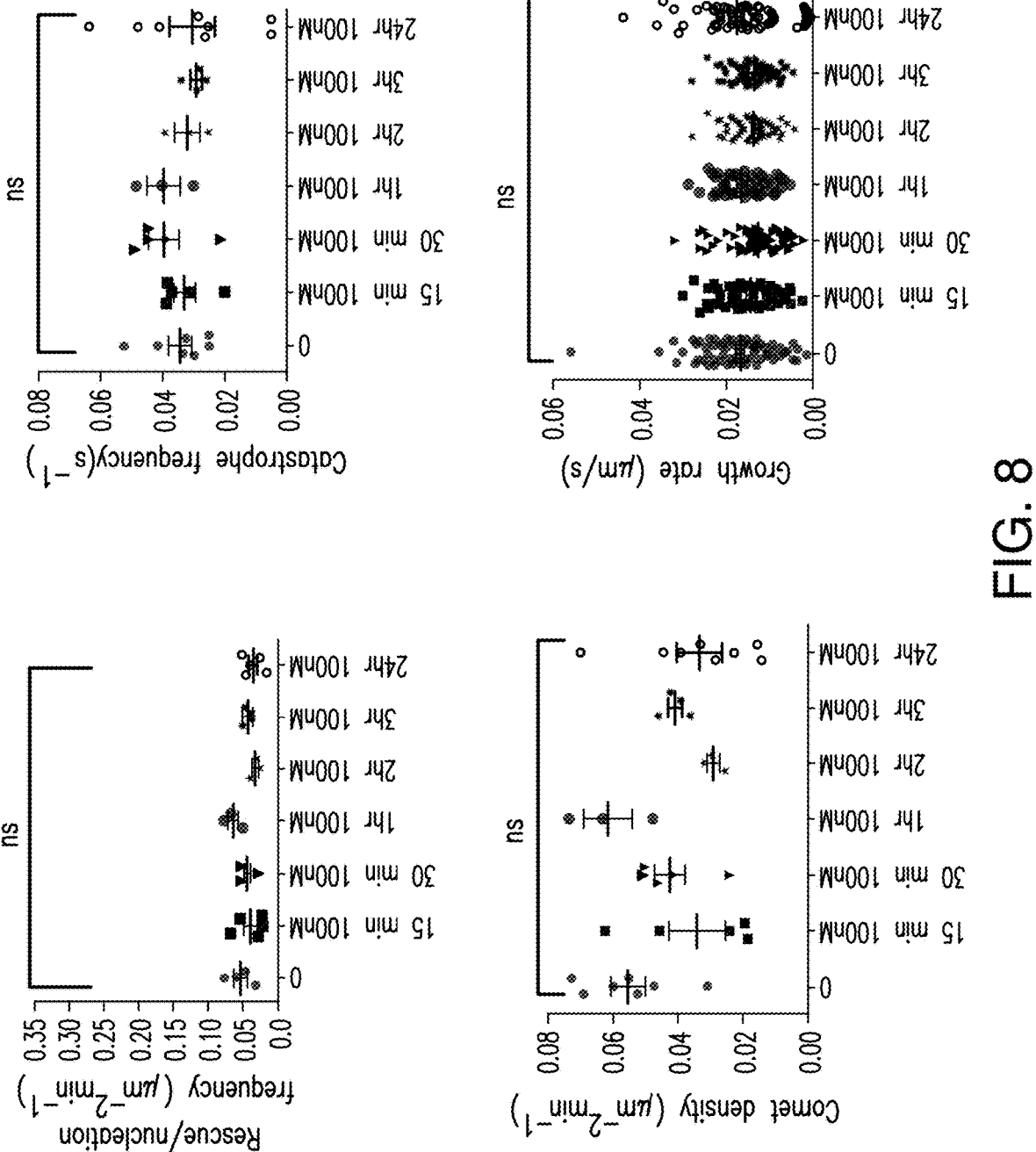
Figures 9A, 9B, 9C, 9D, 9E:
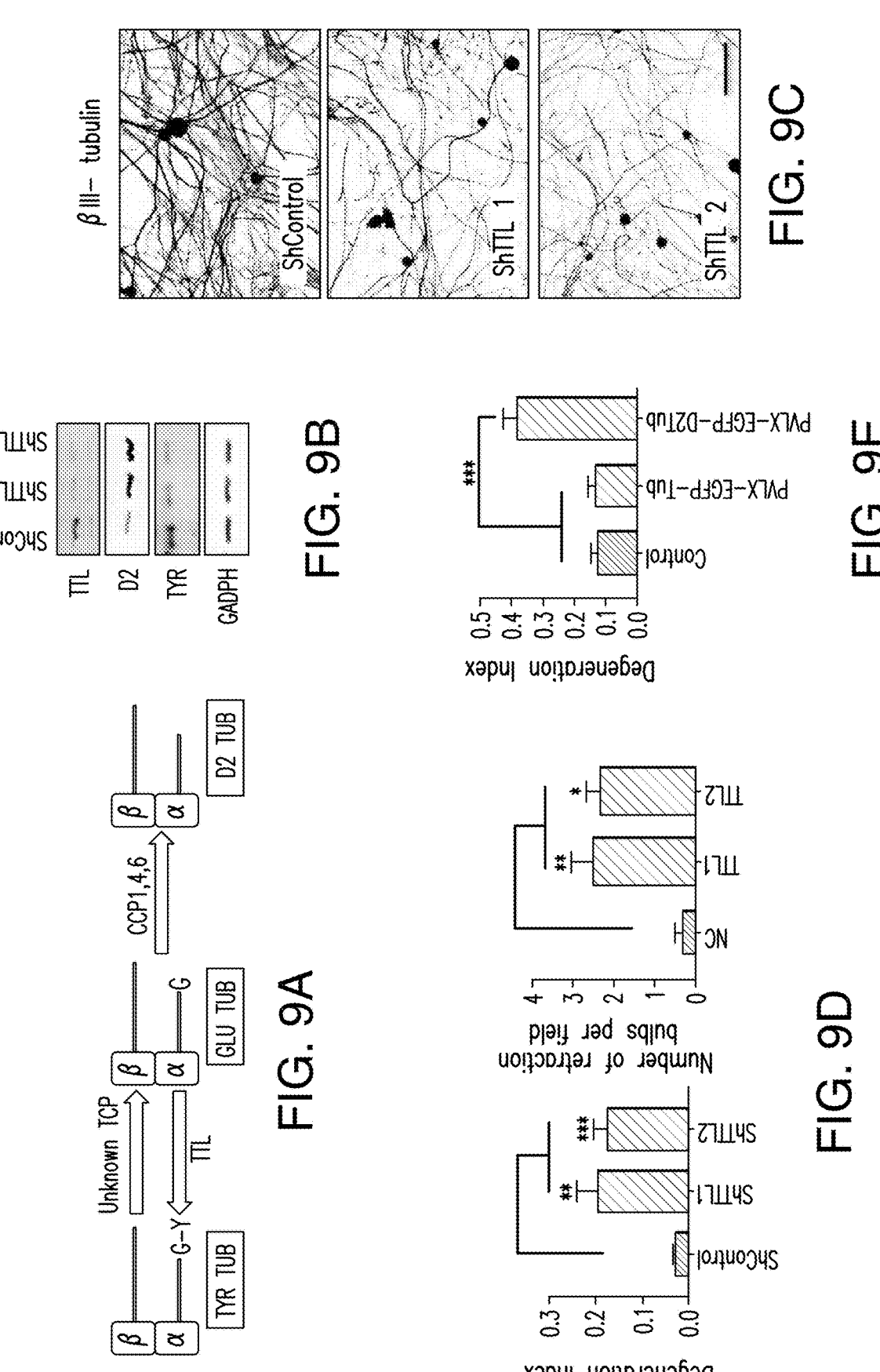
Figure 13E:
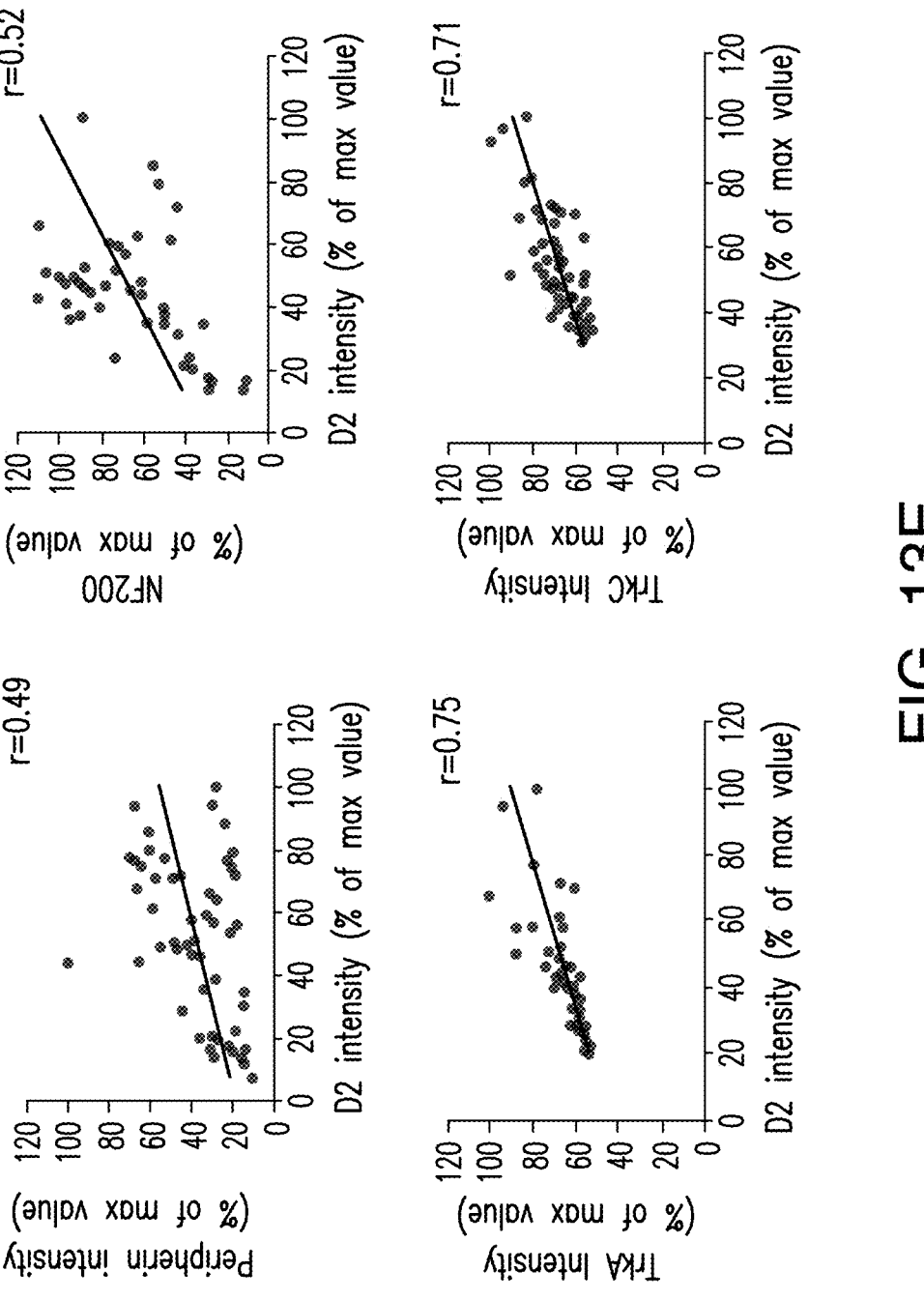
Figures 14A, 14B, 14C, 14D:
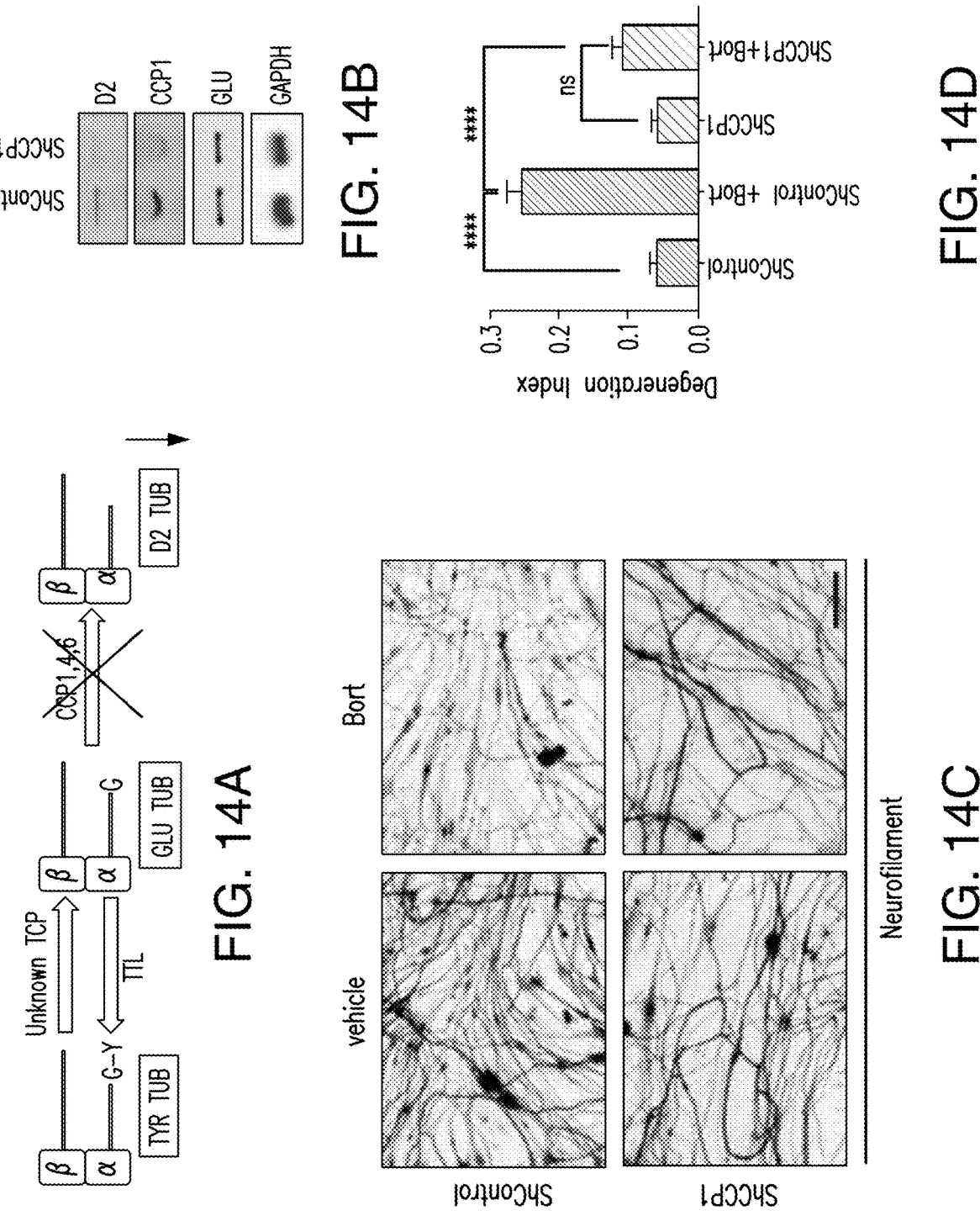

FIG. 8. Bortezomib induces MT stability without affecting MT dynamics prior to D2 induction. EGFP-EB3 time course analysis of MT dynamics parameters in DRG neurons (7 days in vitro (DIV)) treated with 100 nM Bortezomib for the indicated times. Data were pulled from up to 300 comets and 12-15 neurites for each group and analyzed by one-way ANOVA, multiple comparison. (NS, non-significant).

FIG. 9A-9E. Delta-2-tubulin accumulation is sufficient to drive axonopathy. (A) Schematic of the enzymes involved in D2 generation. (B) Immunoblot of tubulin tyrosine ligase (TTL), D2 and tyrosinated (TYR) tubulin levels in adult DRG neurons (14 DIV) silenced of TTL expression at 7 DIV. (C) Representative immunofluorescence images of DRG neurons as in B. (D) Axonal degeneration and number of retraction bulbs per field in DRG neurons treated as in B. (E) Axonal degeneration in DRG neurons that overexpress D2-(PVLX-EGFP-D2Tub) or WT-tubulin (PVLX-EGFP-Tub). Data are mean values±SEM from 3 experiments. *, p≤0.001; , p≤0.01, *p≤0.05 by t-test (unpaired, two-tailed). Bar, 50 sm.

FIG. 10. CCP1 plays a role in DRG axonopathy induced by bortezomib as shown by the knockdown of CCP1 in DRG neurons treated with 100 nM of Bortezomib.

FIG. 11. Immunoblot of tubulin tyrosine ligase (TTL) and D2 levels in adult DRG neurons (14 DIV) treated with 100 nM Bortezomib.

FIG. 12. (A) Immunoblot of D2 levels from whole cell lysates of adult DRG neurons (14 DIV) treated with increasing doses of Bortezomib for the indicated times. (B) IB of D2 levels in the MT pellet (P) and soluble tubulin (S) fractions isolated from adult DRG neurons (8 DIV) treated with 100 nM of Bortezomib for the indicated times.

Figures 13A, 13B, 13C, 13D:
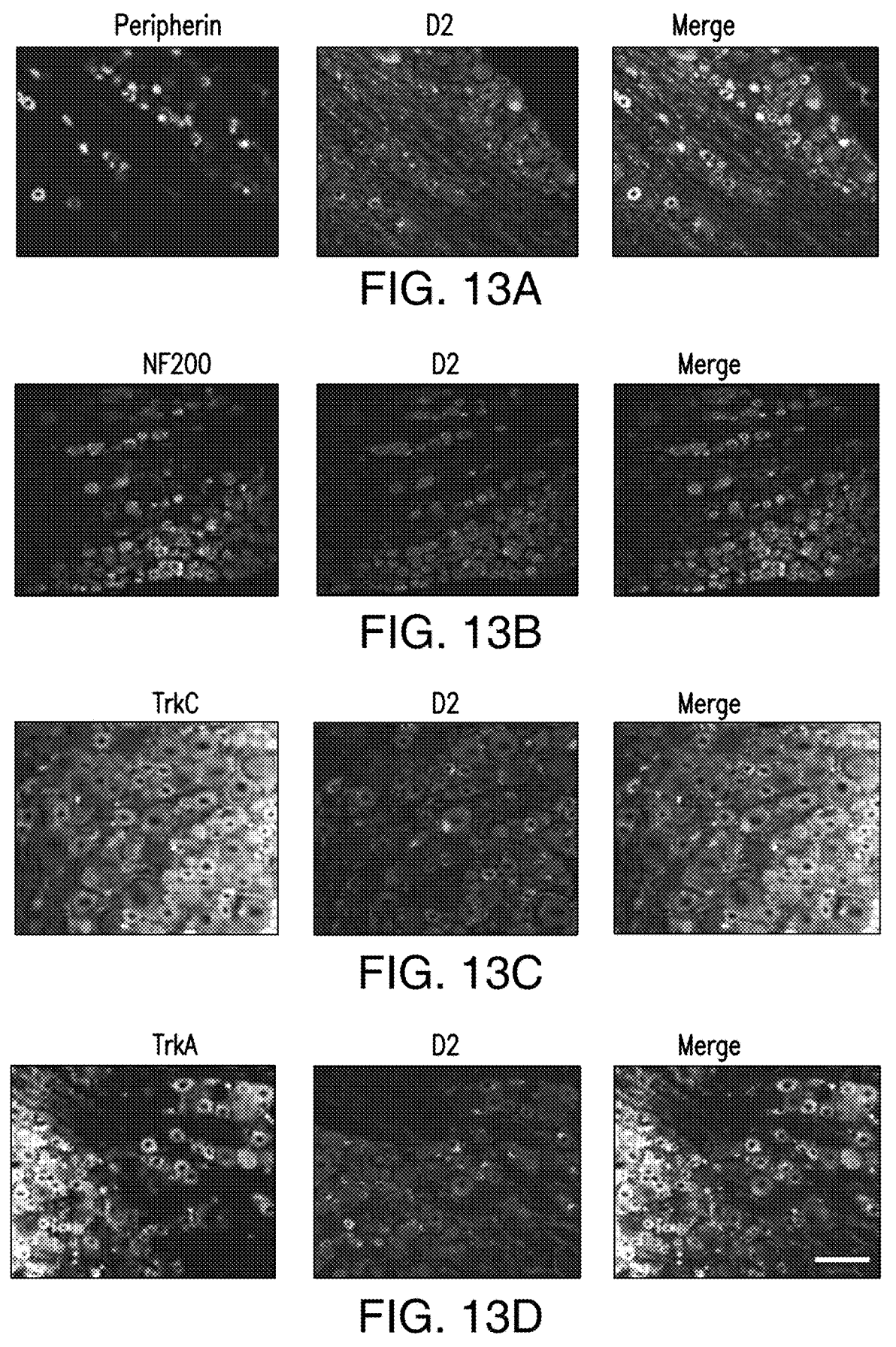

FIG. 13A-13E. Bortezomib accumulates D2 in DRG neurons with different diameter and sensory modalities. (A) Immunofluorescence staining of Peripherin (smaller unmyelinated C-fibers) or (B) NF200 (large myelinated A-$\beta$ fibers)(C) TrkC (proprioceptive)(D) TrkA (nociceptive) in DRG L4-L5 dissected from rats treated with Bortezomib for 24 hr. (E) Correlation between peripherin, NF200, TrkC, TrkA and D2 intensity values in randomly selected DRG cell bodies was calculated by using Pearson coefficient (r). Scale bar, 50 $\mu$m.

FIG. 14A-14D. D2 accumulation is necessary to drive axonopathy by Bortezomib. (A) Schematic of the strategy to inhibit D2 generation by ablating CCP1, the major tubulin carboxypeptidase expressed in DRG neurons. (B) IB of CCP1, D2 and GLU tubulin levels in adult DRG neurons (10 DIV) silenced of CCP1 expression at DIV0. (C) Representative IF images of DRG neurons silenced of CCP1 expression at DIV5 and treated at DIV10 with 100 nM of Bortezomi for 24 h. (D) Axonal degeneration in DRG neurons treated as in C. Data are mean values±SEM from 4 experiments. *, p≤0.001; , p≤0.01; * p≤0.05 by ANOVA. Bar, 50 um.

FIG. 15A-15F. D2 accumulation is necessary and sufficient to affect mitochondria motility. (A) Representative kymographs of mitochondrial motility in DRG neurons (7 DIV) infected for 4 days with PVLX-EGFP-D2- or WT-Tubulin lentivirus prior to 72 hr infection with mito-DsRed lentivirus. (B) Quantification of the percentage of moving mitochondria as in A. Videos (10 s/frame for 30 min). (C, F) Percentage of different mitochondria movement states, Dynamic Pause (DP), Stationary (STA), Anterograde Running (AR), Retrograde Running (RR) (1 s/frame for 3 min, C), (10 s/frame for 30 min, F). (D) Representative kymographs of mitochondrial motility in DRG neurons (7 DIV) infected for 4 days with ShCCP1 or shControl lentivirus prior 72 hr infection with mito-DsRed lentivirus followed by Bortezomib treatment (100 nM for 24 hr). (E) Quantification of the percentage of moving mitochondria as in D. Videos (10 s/frame for 30 min). Data are mean values 1 SEM from 3 (B), 1 (C) and 2 (E and F) experiments. *, p≤0.001; , p≤0.01, *p≤0.05 by ANOVA and unpaired, two-tailed t-test.

5. DETAILED DESCRIPTION

For clarity and not by way of limitation, the detailed description of the present disclosure is divided into the following subsections:

(i) definitions;
(ii) delta-2-tubulin as a biomarker,
(iii) delta-2-tubulin inhibitors;
(iv) pharmaceutical compositions;
(v) methods of use; and
(vi) kits.

5.1 Definitions

The terms used in this specification generally have their ordinary meanings in the art, within the context of the present disclosure and in the specific context where each term is used. Certain terms are discussed below, or elsewhere in the specification, to provide additional guidance to the practitioner in describing the formulations and methods of the disclosed subject matter and how to make and use them.

The term "about" or "approximately" means within an acceptable error range for the particular value as determined by one of ordinary skill in the art, which will depend in part on how the value is measured or determined. i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, a "protein" or "polypeptide" refers to a molecule that includes at least one amino acid residue.

The terms "homology" or "homologous thereto," as used herein, refer to the degree of homology between nucleic acid or amino acid sequences as determined using methods known in the art, for example, but not limited to, software such as BLAST or FASTA.

"Inhibitor" as used herein, refers to a compound or molecule (e.g., small molecule, peptide, peptidomimetic, natural compound, siRNA, anti-sense nucleic acid, aptamer, or antibody) that interferes with (e.g., reduces, prevents, decreases, suppresses, eliminates or blocks) the activity, function, expression and/or generation of a protein or pathway. An inhibitor can be any compound or molecule that changes any activity of a named protein (molecule, any molecule involved with the named molecule or a named associated molecule), such as delta-2-tubulin, CCP1, CCP4 or CCP6, or interferes with the interaction of a named protein, e.g., delta-2-tubulin, with signaling partners or binding partners. Inhibitors also include molecules that indirectly regulate the biological activity of a named protein, e.g., delta-2-tubulin, by intercepting upstream signaling molecules. In certain embodiments, the inhibitor can include molecules that inhibit, minimize and/or reduce the generation and/or production of a named protein such as delta-2-tubulin, e.g., by interfering with the activity and/or function of the enzymes that generate and/or produce delta-2-tubulin (e.g., CCP1, CCP4 or CCP6).

The terms "inhibiting," "eliminating," "decreasing," "reducing" or "preventing," or any variation of these terms, referred to herein, includes any measurable decrease or complete inhibition to achieve a desired result.

As used herein, the term "contacting" a sample with a compound or molecule (e.g., one or more inhibitors, activators and/or inducers) refers to placing the compound in a location that will allow it to touch the sample, e.g., peripheral neurons. The contacting can be accomplished using any suitable methods. For example, contacting can be accomplished by adding the compound to a sample, e.g., contained with a tube or dish. Contacting can also be accomplished by adding the compound to a culture medium that includes the sample.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs;

cats; sheep; pigs; goats; cattle; horses; and non-human primates such as apes and monkeys.

As used herein, the term "treating" or "treatment" (and grammatical variations thereof such as "treat") refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state and remission or improved prognosis. By preventing progression of a disease or disorder, a treatment can prevent deterioration due to a disorder in an affected or diagnosed subject or a subject suspected of having the disorder, but also a treatment can prevent the onset of the disorder or a symptom of the disorder, e.g., peripheral neuropathy, in a subject at risk for the disorder or suspected of having the disorder. In certain embodiments, "treatment" can refer to a decrease in the severity of complications, symptoms and/or cancer or tumor growth. For example, and not by way of limitation, the decrease can be a 10%, 20%, 30%, 40%, 50%, 60%, 70%, 80%, 0.90%, 95%, 98% or 99% decrease in severity of complications, symptoms and/or cancer or tumor growth, for example relative to a comparable control subject not receiving the treatment. In certain embodiments, "treatment" can also mean prolonging survival as compared to expected survival if treatment is not received.

An "effective amount" (or "therapeutically effective amount") is an amount sufficient to affect a beneficial or desired clinical result upon treatment. In certain embodiments, a therapeutically effective amount refers to an amount that is able to achieve one or more of an anti-cancer effect, prolongation of survival and/or prolongation of period until relapse. For example, and not by way of limitation, a therapeutically effective amount can be an amount of a compound (e.g., inhibitor) that that minimizes, prevents, reduces and/or alleviates the symptoms of peripheral neuropathy, e.g., chemotherapy-induced peripheral neuropathy. A therapeutically effective amount can be administered to a subject in one or more doses. The therapeutically effective amount is generally determined by the physician on a case-by-case basis and is within the skill of one in the art. Several factors are typically taken into account when determining an appropriate dosage to achieve a therapeutically effective amount. These factors include age, sex and weight of the subject, the condition being treated, the severity of the condition and the form and effective concentration of the cells administered.

An "anti-cancer agent." as used herein, can be any molecule, compound, chemical or composition that has an anti-cancer effect. Anti-cancer agents include, but are not limited to, chemotherapeutic agents, radiotherapeutic agents, cytokines, anti-angiogenic agents, apoptosis-inducing agents, anti-cancer antibodies and/or agents which promote the activity of the immune system including, but not limited to, cytokines such as but not limited to interleukin 2, interferon, anti-CTLA4 antibody, anti-PD-1 antibody and/or anti-PD-L1 antibody. In certain embodiments, the anti-cancer agent is a platinum-containing compound, e.g., oxaliplatin, cisplatin or carboplatin. Additional non-limiting examples of anti-cancer agents include paclitaxel, eribulin, thalidomide, taxanes, vinca alkaloids and bortezomib. In certain embodiments, the anti-cancer agent is a compound that affects microtubule stability, inhibits the proteasome and/or is an alkylating agent. In certain embodiments, the anti-cancer agent is a chemotherapeutic agent that has been shown to result in peripheral neuropathy, e.g., chemotherapy-induced peripheral neuropathy.

An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer.

5.2 Delta-2-Tubulin as a Biomarker

Certain embodiments provide for delta-2-tubulin as a biomarker for peripheral neuropathy, e.g., chemotherapy-induced peripheral neuropathy. Delta-2-tubulin is a modification of detyrosinated tubulin where the penultimate glutamate is removed (Song and Brady, Trends Cell Biol. 25(3):125-136 (2015), incorporated by reference herein in its entirety).

In a specific, non-limiting embodiment, delta-2-tubulin can be a human delta-2-tubulin protein having an amino acid sequence as set forth in NCBI/UniProtKB Accession No. NP_001180538.1 or an amino acid sequence at least about 95 percent or at least about 98 percent homologous thereto.

In certain embodiments, delta-2-tubulin can be a mouse delta-2-tubulin protein having an amino acid sequence as set forth in NCBI/UniProtKB Accession No. NP 062730.1 or an amino acid sequence at least about 95 percent or at least about 98 percent homologous thereto.

In certain embodiments, a nucleic acid encoding a delta-2-tubulin protein of the present disclosure can include a nucleic acid sequence as set forth in NCBI/UniProtKB Accession No. NM_001193609.1 or a nucleic acid sequence at least about 95 percent or at least about 98 percent homologous thereto.

Delta-2-tubulin can be used as a biomarker to determine if a subject will develop or has developed a peripheral neuropathy, for example, but not limited to, a chemotherapy-induced peripheral neuropathy following treatment with a chemotherapeutic agent. e.g., an anti-cancer agent. A delta-2-tubulin biomarker is a biomarker which manifests as increased delta-2-tubulin expression levels. e.g., in the cell bodies of peripheral neuronal cells, following treatment with an anti-cancer agent, relative to a reference standard level. A reference standard level of delta-2-tubulin can, for example, be established using a reference standard such as cells, e.g., peripheral neuronal cells, from the subject prior to treatment with an anti-cancer agent or in a parallel culture of the subject's cells, e.g., peripheral neuronal cells. Non-limiting examples of peripheral neuronal cells include dorsal root ganglion neurons or a portion of peripheral nerve. In certain embodiments, sural nerves include peripheral neurons. For example, but not by way of limitation, a peripheral nerve biopsy can be performed to obtain tissue for determining relative levels of delta-2-tubulin. In certain embodiments, a biopsy of the sural nerve can be performed to obtain tissue for determining relative levels of delta-2-tubulin. In certain embodiments, a dermal biopsy, which includes epidermal nerve fibers, can be performed to obtain tissue for determining relative levels of delta-2-tubulin.

Methods for determining the localization and/or expression level of a protein biomarker, e.g., delta-2-tubulin, include, but are not limited to, immunofluorescence, immunoglobulin-mediated assays and other techniques known in the art.

In certain, non-limiting embodiments, immunohistochemistry can be used for detecting a delta-2-tubulin biomarker. For example, and not by way of limitation, a first antibody, e.g., an antibody specific for delta-2-tubulin, can be brought into contact with a sample, e.g., a cell or a thin layer of cells, followed by washing to remove unbound antibody, and then contacted with a second, labeled antibody. Labeling can be by fluorescent markers, enzymes, such as peroxidase, avidin or radiolabeling. In certain embodiments, the first antibody can be conjugated to a fluorophore for direct detection. The labeling can be analyzed visually using microscopy and the results can be recorded and/or quantitated.

Various automated sample processing, scanning and analysis systems suitable for use with immunohistochemistry are available in the art. Such systems can include, but are not limited to, automated staining (see, e.g., the Benchmark system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Antibodies for use in the present disclosure include any antibody, whether natural or synthetic, full length or a fragment thereof, monoclonal or polyclonal, that binds sufficiently strongly and specifically to the biomarker that is to be detected. An antibody can have a $K_d$ of at most about $10^{-6}$ M, $10^{-7}$ M, $10^{-8}$ M, $10^{-9}$ M, $10^{-10}$ M, $10^{-11}$ M and $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant.

Antibodies and derivatives thereof that can be used encompasses polyclonal or monoclonal antibodies, chimeric, human, humanized, primatized (CDR-grafted), veneered or single-chain antibodies, phase produced antibodies (e.g., from phage display libraries), as well as functional binding fragments, of antibodies. For example, antibody fragments capable of binding to a biomarker, or portions thereof, including, but not limited to Fv, Fab, Fab' and F(ab')$_2$ fragments can be used. Such fragments can be produced by enzymatic cleavage or by recombinant techniques. For example, and not by way of limitation, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab') heavy chain portion can be designed to include DNA sequences encoding the CH, domain and hinge region of the heavy chain.

In certain embodiments, agents that specifically bind to a polypeptide other than antibodies can be used, such as peptides. Peptides that specifically bind can be identified by any means known in the art, e.g., peptide phage display libraries. Generally, an agent that is capable of detecting a biomarker polypeptide, such that the presence of a biomarker is detected and/or quantitated, can be used. As defined herein, an "agent" refers to a substance that is capable of identifying or detecting a biomarker in a biological sample (e.g., identifies or detects the mRNA of a biomarker, the DNA of a biomarker or the protein of a biomarker). In certain embodiments, the agent is a labeled or a labelable peptide, which specifically binds to a biomarker polypeptide.

5.3 Delta-2-Tubulin Inhibitors

Non-limiting examples of delta-2-tubulin inhibitors include compounds, molecules, chemicals, polypeptides and proteins that inhibit and/or reduce the expression, generation, function and/or activity of delta-2-tubulin.

Non-limiting examples of delta-2-tubulin inhibitors include ribozymes, antisense oligonucleotides, shRNA molecules and siRNA molecules that specifically inhibit and/or reduce the expression or activity of delta-2-tubulin. One non-limiting example of a delta-2-tubulin inhibitor includes an antisense, shRNA or siRNA nucleic acid sequence homologous to at least a portion of a delta-2-tubulin nucleic acid sequence, wherein the homology of the portion relative to the delta-2-tubulin sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion can constitute at least 10 nucleotides or at least 15 nucleotides or at least 20 nucleotides or at least 25 nucleotides or at least 30 nucleotides and the antisense nucleic acid, shRNA or siRNA molecules can be up to 15 or up to 20 or up to 25 or up to 30 or up to 35 or up to 40 or up to 45 or up to 50 or up to 75 or up to 1×) nucleotides in length. Antisense, shRNA or siRNA molecules can include DNA or atypical or non-naturally occurring residues, for example, but not limited to, phosphorothioate residues.

The RNA molecules of the present disclosure can be expressed from a vector or produced chemically or synthetically. Methods for selecting an appropriate dsRNA or dsRNA-encoding vector are well known in the art for genes whose sequence is known (e.g., see Tuschl. T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and PCT Patent Application Nos. WO 2001/036646, WO 1999/032619 and WO 2001/068836, the contents of which are incorporated by reference herein in their entireties).

In certain non-limiting embodiments, the delta-2-tubulin inhibitor can be a small molecule, peptide, an antibody or antibody fragment that can partially or completely block delta-2-tubulin activity, organization, production and/or localization.

In certain embodiments, a delta-2-tubulin inhibitor can be an agent, e.g., RNA molecule, compound, polypeptide, antibody and small molecule, that inhibits and/or activates an enzyme that plays a role in delta-2-tubulin production (see FIG. 9). For example, but not by way of limitation, a delta-2-tubulin inhibitor can be an inhibitor of CCP1, CCP4 or CCP6, e.g., an inhibitor of CCP1. In certain embodiments, the delta-2-tubulin inhibitor can be an activator of tubulin tyrosine ligase (TTL).

5.4 Pharmaceutical Compositions

The present disclosure provides for pharmaceutical formulations of the delta-2-tubulin inhibitors disclosed above in section 5.3 for therapeutic use. In certain embodiments, the pharmaceutical formulation includes a delta-2-tubulin inhibitor and a pharmaceutically acceptable carrier. In certain embodiments, a pharmaceutical composition of the present disclosure can include an inhibitor of an enzyme that generates delta-2-tubulin and a pharmaceutically acceptable carrier.

"Pharmaceutically acceptable carrier," as used herein, includes any carrier which does not interfere with the effectiveness of the biological activity of the active ingredients, e.g., inhibitors, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioabsorbable matrix materials, implantation elements containing the inhibitor and/or any other suitable vehicle, delivery or dispensing means or material. Such carriers can be formulated by conventional methods and can be administered to the subject. In certain embodiments, the pharmaceutical acceptable carrier can include buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, a suitable pharmaceutically acceptable carrier can include one or more of water, saline, phosphate buffered saline, dextrose, glycerol, ethanol or combinations thereof.

In certain non-limiting embodiments, the pharmaceutical formulations can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral or nasal ingestion by a patient to be treated. In certain embodiments, the pharmaceutical formulation can be a solid dosage form. In certain embodiments, the tablet can be an immediate release tablet. Alternatively or additionally, the tablet can be an extended or controlled release tablet. In certain embodiments, the solid dosage can include both an immediate release portion and an extended or controlled release portion.

In certain embodiments, the pharmaceutical formulations can be formulated using pharmaceutically acceptable carriers well known in the art that are suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. For example, and not by way of limitation, formulations of the present disclosure can be administered to the patient intravenously in a pharmaceutically acceptable carrier such as physiological saline. In certain embodiments, the present disclosure provides a parenteral formulation that includes a delta-2-tubulin inhibitor. In certain embodiments, the present disclosure provides a parenteral formulation that includes an inhibitor of CCP1, CCP4 or CCP6. In certain embodiments, a parenteral formulation of the present disclosure can include an inhibitor of CCP1. In certain embodiments, a parenteral formulation of the present disclosure can include an activator of tubulin tyrosine ligase (TTL). In certain embodiments, the present disclosure provides a parenteral formulation that includes one or more of the inhibitors and/or activators disclosed herein.

Standard methods for intracellular delivery can be used (e.g., delivery via liposome). Such methods are well known to those of ordinary skill in the art. Therapeutic administration of an inhibitor intracellularly can also be accomplished using gene therapy, e.g., by using shRNAs. The route of administration eventually chosen will depend upon a number of factors and can be ascertained by one skilled in the art.

In certain embodiments, the pharmaceutical formulations can include an active ingredient, e.g., delta-2-tubulin inhibitor, in a therapeutically effective amount. In certain embodiments, the pharmaceutical formulations can include an inhibitor of CCP1, CCP4 or CCP6, e.g., an inhibitor of CCP1, in a therapeutically effective amount. In certain embodiments, the pharmaceutical formulations can include an activator of tubulin tyrosine ligase (TTL) in a therapeutically effective amount. The therapeutically effective amount of an active ingredient can vary depending on the active ingredient, e.g., delta-2-tubulin inhibitor, formulation used and the age, weight, etc. of the subject to be treated. In certain embodiments, a patient can receive a therapeutically effective amount of a delta-2-tubulin inhibitor in single or multiple administrations of one or more formulations, which can depend on the dosage and frequency as required and tolerated by the patient.

In certain non-limiting embodiments, the delta-2-tubulin inhibitors described above can be used alone or in combination with one or more anti-cancer agents. In certain non-limiting embodiments, an inhibitor of CCP1, CCP4 or CCP6 can be used alone or in combination with one or more anti-cancer agents. "In combination with," as used herein, means that a delta-2-tubulin inhibitor and the one or more anti-cancer agents are administered to a subject as part of a treatment regimen or plan. In certain embodiments, being used in combination does not require that the inhibitor and the one or more anti-cancer agents are physically combined prior to administration or that they be administered over the same time frame. Accordingly, the anti-cancer agent can be administered prior to, concurrently with, or subsequent to, administration of one or more doses of an active ingredient, e.g., a delta-2-tubulin inhibitor or an inhibitor of CCP1, CCP4 or CCP6. In certain embodiments, the anti-cancer agent is a platinum-containing compound, e.g., oxaliplatin, cisplatin or carboplatin, paclitaxel, eribulin, thalidomide, taxanes, vinca alkaloids, bortezomib, a compound that affects microtubule stability, a compound that affects mitochondrial movement, a compound that inhibits the proteasome, a compound that is an alkylating agent and/or a chemotherapeutic agent that has been shown to result in peripheral neuropathy, e.g., chemotherapy-induced peripheral neuropathy.

5.5 Methods of Use

The present disclosure provides for methods of identifying subjects that are at risk at developing or that have developed neuropathy, e.g., chemotherapy-induced peripheral neuropathy (CIPN) by detection of delta-2-tubulin expression levels. The present disclosure further provides for methods of reducing and/or inhibiting delta-2-tubulin production, activity and/or expression levels by the administration of a delta-2-tubulin inhibitor. Still further, certain embodiments provide for methods of reducing and/or inhibiting delta-2-tubulin activity and/or production and/or expression levels by the administration of an effective amount of a compound that inhibits delta-2-tubulin formation (e.g., an inhibitor or an antagonist of CCP1, CCP4 or CCP6 or an activator of TTL) or promotes formation or retention of another form of tubulin. For example, but not by way of limitation, a method of the present disclosure can include an inhibitor or an antagonist of CCP1. As such, the present disclosure relates to methods for inhibiting and/or reducing delta-2-tubulin expression, production, functionality and/or activity to reduce and/or prevent neuropathy in a subject.

The present disclosure further provides for assays to identify anti-cancer agents that do not result in neuropathy, e.g., CIPN, and to identify compounds that can be used to prevent and/or treat neuropathy, e.g., CIPN. Non-limiting examples of delta-2-tubulin inhibitors, and pharmaceutical formulations thereof, are disclosed in sections 5.3 and 5.4 above.

In certain non-limiting embodiments, a sample includes, but is not limited to, a clinical sample, cells in culture, cell supernatants, cell lysates and tissue samples. The source of the sample can be solid tissue (e.g., from a fresh, frozen, and/or preserved organ, tissue sample, biopsy or aspirate) or cells, e.g., from the peripheral nervous system, from the individual. In certain non-limiting embodiments, the sample is one or more peripheral neuronal cells. In certain non-limiting embodiments, the sample is one or more dorsal root ganglion neuronal cells. In certain non-limiting embodiments, the sample is a biopsy of a sural nerve of the subject. In certain non-limiting embodiments, the sample is a biopsy of the dermis of the subject. In certain embodiments, the sample can be a biopsy of any tissue that contains peripheral neurons.

5.5.1 Biomarker Methods

Certain non-limiting embodiments provide for a method of determining whether a subject will develop peripheral neuropathy upon treatment with an anti-cancer agent. In certain embodiments, a method of the present disclosure can include detecting a delta-2-tubulin biomarker in a sample of a patient, where if the delta-2-tubulin biomarker is increased following treatment with an anti-cancer agent as compared to a control, it is more likely that the patient will develop, e.g., at an increased risk of developing, peripheral neuropathy, e.g., chemotherapy-induced peripheral neuropathy, upon treatment with the anti-cancer agent.

In certain non-limiting embodiments, the method for determining whether a subject will develop peripheral neuropathy, e.g., chemotherapy-induced peripheral neuropathy, includes, obtaining a sample from the subject before treatment of the subject with an anti-cancer agent, and determining, in the sample, the effect of treatment with the anti-cancer agent on the expression level of a delta-2-tubulin biomarker, where if the delta-2-tubulin biomarker expression level is not increased following treatment with the anti-cancer agent, then the subject will likely not develop, e.g., at a reduced risk of developing, chemotherapy-induced peripheral neuropathy upon treatment with the anti-cancer agent. In certain embodiments, the method can further include treating the subject with the anti-cancer agent.

Certain non-limiting embodiments provide for a method for determining whether a subject will develop peripheral neuropathy, e.g., chemotherapy-induced peripheral neuropathy, can include, obtaining a sample from the subject before treatment of the subject with an anti-cancer agent, and determining, in the sample, the effect of treatment with the anti-cancer agent on the expression level of a delta-2-tubulin biomarker, where if the delta-2-tubulin biomarker expression level is increased following treatment with the anti-cancer agent, then the subject will likely develop chemotherapy-induced peripheral neuropathy upon treatment with the anti-cancer agent. In certain embodiments, the method can further include initiating treatment of the subject with another modality, for example, an alternative chemotherapeutic agent, biologic anticancer agent or radiation therapy.

Certain non-limiting embodiments provide for a method for determining whether a subject has developed peripheral neuropathy, e.g., chemotherapy-induced peripheral neuropathy, which can include, obtaining a sample from the subject after treatment with an anti-cancer agent, and determining, in the sample, the expression level of a delta-2-tubulin biomarker, where if the delta-2-tubulin biomarker expression level is increased following treatment with the anti-cancer agent as compared to a reference sample, then the subject has developed chemotherapy-induced peripheral neuropathy. In certain embodiments, the method can further include stopping treatment with the anti-cancer agent and initiating treatment of the subject with another modality, for example, an alternative chemotherapeutic agent, biologic anticancer agent or radiation therapy.

Certain non-limiting embodiments provide for a method for determining whether a subject has developed peripheral neuropathy, e.g., chemotherapy-induced peripheral neuropathy, which can include, obtaining a sample from the subject after treatment with an anti-cancer agent, and determining, in the sample, the expression level of a delta-2-tubulin biomarker, where if the delta-2-tubulin biomarker expression level is not increased following treatment with the anti-cancer agent as compared to a reference sample, then the subject has not developed chemotherapy-induced peripheral neuropathy. In certain embodiments, the method can further include continuing or resuming treatment of the subject with a therapeutically effective amount of the anti-cancer agent.

In certain embodiments, the sample can be a biopsy of a peripheral nerve. For example, but not by way of limitation, the sample can be a biopsy of a sural nerve of the subject. In certain non-limiting embodiments, the sample is a biopsy of the dermis of the subject.

Any of the foregoing methods can include collecting one or more samples from the subject, where the samples from the subject can be used to determine the effect of an anti-cancer agent on the expression level of a delta-2-tubulin biomarker.

5.5.2 Methods of Treatment

Certain embodiments further provide for methods for the treatment of neurodegeneration of the peripheral nervous system. Certain non-limiting embodiments provide for a method for the treatment of chemotherapy-induced peripheral neuropathy in a subject. In certain embodiments, the method includes administering a therapeutically effective amount of a delta-2-tubulin inhibitor or a compound that inhibits and/or reduces the expression, generation, function and/or activity of delta-2-tubulin to a subject, e.g., a subject that is being treated with an anti-cancer agent or has been treated with an anti-cancer agent. Alternatively or additionally, the method includes administering a therapeutically effective amount of an inhibitor of CCP1, CCP4 or CCP6. In certain embodiments, the delta-2-tubulin inhibitor or inhibitor of CCP1, CCP4 or CCP6 can be administered before, during or after administration of an anti-cancer agent. In certain embodiments, the delta-2-tubulin inhibitor or inhibitor of CCP1, CCP4 or CCP6 can be administered in the absence of an anti-cancer agent. In certain embodiments, the method can include administering a therapeutically effective amount of an activator of tubulin tyrosine ligase (TTL).

In certain embodiments, a method for the treatment of peripheral neuropathy, e.g., chemotherapy-induced peripheral neuropathy, in a subject can include detecting the expression level of delta-2-tubulin in a sample obtained from the subject. For example, and not by way of limitation, a method for the treatment of chemotherapy-induced peripheral neuropathy in a subject can include obtaining a sample from the subject after treatment with an anti-cancer agent, and determining, in the sample, the expression level of a delta-2-tubulin biomarker, where if the delta-2-tubulin biomarker expression level is increased following treatment with the anti-cancer agent as compared to a reference sample, then initiating treatment of the subject with a delta-2-tubulin inhibitor or an inhibitor of CCP1, CCP4 or CCP6. In certain embodiments, a treatment method disclosed herein can include the administration of an agonist or activator of Tubulin-tyrosine ligase (TTL). Alternatively and/or additionally, the methods can include the administration of a compound identified by the assays disclosed herein in the absence of a delta-2-tubulin inhibitor or in combination with a delta-2-tubulin inhibitor.

Certain embodiments further provide for a method for preventing and/or minimizing the development of peripheral neuropathy, e.g., chemotherapy-induced peripheral neuropathy, in a subject. For example, and not by way of limitation, the method can include (1) obtaining a sample from the subject prior to treatment with an anti-cancer agent, (2) contacting the sample with the anti-cancer agent and (3) determining, in the sample, the expression level of a delta-2-tubulin biomarker, where if the delta-2-tubulin biomarker expression level is increased following treatment with the anti-cancer agent as compared to a reference sample, then treating the subject with a combination therapy that includes a delta-2-tubulin inhibitor (or an inhibitor of CCP1, CCP4 or CCP6 or an activator of tubulin tyrosine ligase) and an anti-cancer agent. In certain embodiments, the inhibitor, e.g., delta-2-tubulin inhibitor, can be administered prior to, concurrently with and/or after administration of the anti-cancer agent.

Certain embodiments provide for a method for preventing and/or minimizing the development of peripheral neuropathy, e.g., chemotherapy-induced peripheral neuropathy, in a subject. For example, and not by way of limitation, the method can include (1) obtaining a sample from the subject prior to treatment with an anti-cancer agent, (2) contacting the sample with the anti-cancer agent and (3) determining, in the sample, the expression level of a delta-2-tubulin biomarker, where if the delta-2-tubulin biomarker expression level is not increased following treatment with the anti-cancer agent as compared to a reference sample, then treating the subject with the anti-cancer agent in the absence of the delta-2-tubulin inhibitor.

Certain non-limiting embodiments provide for a method of treating peripheral neuropathy in a subject that includes administering an effective amount of an inhibitor of delta-2-tubulin or an effective amount of a compound that inhibits delta-2-tubulin formation (e.g., an inhibitor or an antagonist of CCP1, CCP4 or CCP6 or an activator of tubulin tyrosine ligase).

The treatments can be administered by any route known in the art, including, but not limited to, local instillation or placement of an implant containing therapeutic agent, intrathecal, subcutaneous, intravenous, oral, etc.

5.5.3 Assays

Certain embodiments provide for assays for identifying anti-cancer agents that have a reduced risk in causing peripheral neuropathy, e.g., as measured by an increase delta-2-tubulin expression and/or activity following treatment with the anti-cancer agent. For example, and not by way of limitation, an assay can be used to identify compounds that can be used as an anti-cancer agent and have a reduced risk for inducing chemotherapy-induced peripheral neuropathy. In certain embodiments, the assay for identifying an anti-cancer agent that has a reduced risk of inducing peripheral neuropathy can include contacting a sample, e.g., cultured peripheral neuronal cells, with a drug candidate, and detecting the expression level of delta-2-tubulin, where if the drug candidate does not increase the expression level of delta-2-tubulin as compared to a reference sample, then the drug candidate has a reduced risk of inducing chemotherapy-induced peripheral neuropathy in a subject that will be treated with the drug candidate. In certain embodiments, if the drug candidate results in an increase in the expression level of delta-2-tubulin as compared to a reference sample, then the drug candidate has an increased risk in inducing peripheral neuropathy in a subject. In certain embodiments, the drug candidate is an FDA-approved chemotherapeutic agent. In certain embodiments, the drug candidate is a novel compound or newly identified chemotherapeutic agent.

Certain embodiments further provide for assays for identifying compounds that can be used to treat peripheral neuropathy, e.g., chemotherapy-induced peripheral neuropathy. In certain embodiments, an assay can be used to identify compounds that can reduce delta-2-tubulin expression and/or activity that is present during neuropathy, e.g., chemotherapy-induced peripheral neuropathy, following treatment with an anti-cancer agent and/or prevent an increase in delta-2-tubulin expression and/or activity during treatment with an anti-cancer agent. In certain embodiments, the method includes (1) contacting a sample, e.g., cultured peripheral neuronal cells, with an anti-cancer agent that has been shown to induce chemotherapy-induced peripheral neuropathy, (2) detecting the expression level of delta-2-tubulin to confirm the induction of chemotherapy-induced peripheral neuropathy, (3) treatment of the sample with a drug candidate and (4) detecting the expression of delta-2-tubulin in the sample after treatment of the sample with a drug candidate, where if the expression level of delta-2-tubulin decreases after treatment with the drug candidate, then the drug candidate can be an effective compound for treating peripheral neuropathy, e.g., chemotherapy-induced peripheral neuropathy, in a subject. In certain embodiments, the method for identifying compounds that can be used to prevent and/or minimize peripheral neuropathy can include (1) contacting a sample, e.g., cultured peripheral neuronal cells, with a drug candidate, (2) contacting the drug candidate-treated sample with an anti-cancer agent that has been shown to induce chemotherapy-induced peripheral neuropathy and (3) detecting the expression level of delta-2-tubulin in the drug candidate and anti-cancer agent treated sample, where if the expression level of delta-2-tubulin does not increase after treatment with the anti-cancer agent, then the drug candidate can be an effective compound for preventing and/or minimizing the occurrence of chemotherapy-induced peripheral neuropathy in a subject.

In certain embodiments, the disclosed assays can be used to screen large libraries of compounds. In certain non-limiting embodiments, the assays of the present disclosure can be used to prioritize large numbers of new compounds for further drug development and/or can identify new compounds that can be used in combination with compounds currently being used clinically. Candidate compounds (also referred to herein as drug candidates) to be screened in the currently disclosed assays include pharmacologic agents already known in the art as well as compounds previously unknown to have any pharmacological activity. One non-limiting example of a library that includes compounds that can be screened using the disclosed assays is an FDA approved library of compounds that can be used by humans.

In various embodiments, the assays can be performed in multiwell formats, in microtiter plates, in multispot formats or in arrays. In certain non-limiting embodiments, the cells for use in the present disclosure can be cultured, grown and/or analyzed in 96-well microtiter plates. In certain non-limiting embodiments, the cells for use in the present disclosure can be cultured, grown and/or analyzed in 384-well microtiter plates.

5.6 Kits

Certain embodiments further provide for kits that can be used to practice the foregoing methods. For example, and not by way of limitation, a kit can provide for detecting the expression level and/or localization of a delta-2-tubulin biomarker. Delta-2-tubulin and methods for measuring delta-2-tubulin levels are described in the sections above.

Types of kits include, but are not limited to, arrays/microarrays, biomarker-specific antibodies and beads, which further contain one or more probes, antibodies, or other detection reagents for detecting a delta-2-tubulin biomarker.

In non-limiting embodiments, a kit can include at least one antibody for immunodetection of the biomarker(s) to be identified. Antibodies, both polyclonal and monoclonal, including molecules that include an antibody variable region, specific for a delta-2-tubulin biomarker, can be prepared using conventional immunization techniques, as will be generally known to those of skill in the art. The immunodetection reagents of the kit can include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels ($^{3}$H, $^{33}$S, $^{32}$P, $^{14}$C and $^{131}$I) or enzymes (alkaline phosphatase, horseradish peroxidase). Alternatively, a detectable moiety can be included in a secondary antibody or antibody fragment which selectively binds to the first antibody or antibody fragment (where said first antibody or antibody fragment specifically recognizes delta-2-tubulin).

In certain non-limiting embodiments, a kit can provide for comparing the delta-2-tubulin biomarker with a reference standard. For example, in certain non-limiting embodiments, the kit can further include a probe, microarray or antibody suitable for detecting protein that can be used a control for normalizing protein expression levels. Non-limiting examples of such proteins include β-III-tubulin.

A kit can further include instructions for using the kit to determine and/or evaluate the localization and/or expression level of a delta-2-tubulin biomarker. Specifically, in certain embodiments, the instructions can describe that a higher expression level of delta-2-tubulin in peripheral nerve cell bodies following treatment with an anti-cancer agent, as compared to a reference control, is indicative that the subject will likely have neuropathy.

Certain embodiments further provide kits that include a delta-2-tubulin inhibitor or a formulation that includes a therapeutically effective amount of a delta-2-tubulin inhibitor. In certain embodiments, a kit of the present disclosure includes an inhibitor or an antagonist of CCP1, CCP4 or CCP6 or an activator of tubulin tyrosine ligase. In certain embodiments, a kit of the present disclosure can include a formulation that includes a therapeutically effective amount of an inhibitor or an antagonist of CCP1, CCP4 or CCP6 or an activator of tubulin tyrosine ligase.

In certain embodiments, a kit of the present disclosure can further include an anti-cancer agent, e.g., within the same container as the delta-2-tubulin inhibitor (or formulation thereof) or within a second container. For example, and not by way of limitation, the anti-cancer agent can be a platinum-containing compound, e.g., oxaliplatin, cisplatin or carboplatin, paclitaxel, eribulin, thalidomide, taxanes, vinca alkaloids and bortezomib.

In non-limiting embodiments, a kit for performing an above-described assay is provided. For example, and not by way of limitation, a kit is provided for determining whether a drug candidate produces an anti-cancer effect without increasing delta-2-tubulin expression and/or activity. In certain embodiments, the kit can include one or more drug candidates and/or a provision for detecting the expression level and/or localization of a delta-2-tubulin biomarker and/or one or more cells, e.g., peripheral neuronal cells.

The following examples are offered to more fully illustrate the disclosure but are not to be construed as limiting the scope thereof.

6. EXAMPLE 1: INDUCTION OF DELTA-2-TUBULIN RESULTS IN AXONOPATHY

To determine the effects of bortezomib on the post-translation modifications of tubulin, female Wistar rats were treated with single or multiple administrations pf bortezomib (5 rats for each treatment). Acute treatment included a single intravenous administration of bortezomib at a concentration of 0.2 mg/kg. Chronically treated rats were treated with bortezomib for a total of 8 weeks, with administration of bortezomib three times per week at a concentration of 0.2 mg/kg. As shown in FIG. 1, chronic doses of bortezomib affected animal behavior and nerve function as determined by the dynamic test, planar test and electrophysiological tests. The dynamic test shows the hind-paw withdrawal response to mechanical stimulus (10-50 g) and the plantar test shows the plantar withdrawal latency response to heat source (infra-red light). Certain post-translation modifications of α-tubulin, e.g., acetylation, are reduced in dorsal root ganglions neurons (DRGs) and sural nerves (SNs) from rats chronically treated with bortezomib (FIG. 2) and in rats acutely treated with bortezomib (FIG. 3).

To determine the effect of bortezomib on tubulin expression, DRGs were analyzed for delta-2-tubulin expression. Bortezomib acutely increased delta-2-tubulin in DRG cell bodies under acute treatment (FIG. 3) and under chronic treatment (FIG. 2) as compared to βIII-tubulin and the control cells. Further analysis of other unrelated chemotherapy-induced peripheral neuropathy (CIPN) drugs was performed to determine their effect on delta-2-tubulin expression levels. As shown in FIG. 4, paclitaxel and cisplatin acutely accumulated delta-2-tubulin in DRG neurons as compared to the control. Additional experiments were performed to determine whether DRGs with different sensory modalities and diameters are preferentially affected by bortezomib treatment. As shown in FIG. 13, proprioceptive and nociceptive DRG neurons, which have different sensory modalities, accumulate delta-2-tubulin after treatment with bortezomib.

Peripheral neurons from patients suffering from CIPN were analyzed for delta-2-tubulin expression. As shown in FIG. 5, bortezomib induced delta-2-tubulin expression in peripheral neurons, e.g., in the sural nerve, in CIPN patients. In cultured hippocampal and DRG neurons, treatment with bortezomib or paclitaxel resulted in an increase in delta-2-tubulin expression (FIG. 6). As shown in FIG. 7, bortezomib induced delta-2-tubulin at the onset of axonal degeneration as determined by the degeneration index. In addition. FIG. 12A shows the accumulation of delta-2-tubulin in DRG neurons and FIG. 12B shows that over the time course of bortezomib treatment, the level of delta-2-tubulin was observed to increase in the microtubule fraction (P) isolated from DRG neurons.

Microtubule dynamics were analyzed in DRG neurons following bortezomib treatment. As shown in FIG. 8, bortezomib does not affect microtubule dynamics prior to delta-2-tubulin induction in DRG neurons as determined by rescue/nucleation frequency, catastrophe frequency, comet density and growth rate. To determine if the accumulation of delta-2-tubulin is sufficient to drive axonopathy, peripheral neurons were treated with a short hairpin RNA targeting Tubulin-tyrosine ligase (TL). TTL binds αβ-tubulin dimer and catalyzes the post-translational addition of a tyrosine to the C-terminal end of detyrosinated α-tubulin. Song et al., J. of Bio. Chem. 290(23):14765-14775 (2015). As shown in FIG. 9, the knockdown of TTL activity resulted in the accumulation of delta-2-tubulin and in the degeneration of peripheral neurons. Further, as shown in FIG. 11, western blot analysis confirmed the accumulation of delta-2-tubulin and the reduction of TTL expression in DRG neurons following bortezomib treatment.

Without being bound to a particular theory, these data show that the pathogenic mechanisms of CIPN drugs can converge on the acute induction of delta-2-tubulin and, potentially, additional tubulin post-translation modifications. In addition, subtype-specific DRG sensitivity differs among CIPN drugs. Without being bound to a particular theory, it appears that induction of delta-2-tubulin by bortezomib can be related to the regulation of the enzymes that catalyze tubulin modification, rather than a change in microtubule behavior. Further, the accumulation of delta-2-tubulin was sufficient to drive axonopathy.

7. EXAMPLE 2: PATHOGENIC ROLE FOR MICROTUBULE REGULATING PATHWAYS IN CHEMOTHERAPY INDUCED PERIPHERAL NEUROPATHY

Emerging studies from several groups have indicated that dynamic microtubules, typically deprived of tubulin post-translational modifications (PTMs) associated with microtubule longevity, play key roles in neuronal function. In addition, synaptic biphasic fluctuations of microtubule instability/stability and tubulin PTMs have recently been associated with memory formation and are disrupted in aging, indicating a primary role for the regulation of microtubule dynamics and tubulin PTMs in the maintenance of synaptic plasticity. In support of this model, it was recently found that stabilization of dynamic microtubules and induction of tubulin PTMs by the formin mDial contribute to oligomeric AD 1-42 synaptotoxicity, and inhibition of microtubule dynamics alone is sufficient to promote tau hyperphosphorylation and tau dependent synaptotoxicity (Qu et al., J Cell Biol, 2017). To test whether these changes occur at synapses and are directly responsible for synapse loss, microscopy assays were further developed that measure microtubule invasions into dendritic spines and microtubule contacts with single presynaptic boutons of hippocampal and cortical neurons in culture. These assays are currently being used to investigate the temporal and spatial nature of these changes in the intact synapse upon modulation of synaptic activity and before and after treatment with oligomeric Aβ1-42. These exciting findings are in line with a parallel study in which we are testing whether undesired fluctuations in microtubule stability/dynamics and tubulin PTMs are primary to axonal neurodegeneration induced by chemotherapeutic agents in sensory neurons using in vitro and in vivo models of disease. Altogether, these studies introduce a novel activity for formins in Aβ1-42 neurotoxicity through stabilization of dynamic microtubules in neurons, and demonstrate an unforeseen role for dynamic changes in microtubule behavior in regulating tau metabolism, axonal integrity and synaptic function.

8. EXAMPLE 3: CCP1 PLAYS A ROLE IN DRG AXONOPATHY

CCP1 is a tubulin enzyme that participates in the generation of delta-2 tubulin (FIG. 9). To determine the importance of CCP1 in neuropathy upon treatment with a chemotherapy agent, DRGs were treated with 200 mM bortezomib in vitro for 24 hrs. DRGs were also treated with a short hairpin RNA targeting CCP1. As shown in FIG. 10 and FIG. 14, the knockdown of CCP1 activity prevented accumulation of delta-2 tubulin and prevented DRG axonopathy that occurs upon treatment with bortezomib. These data are supportive of a pathogenic role of delta-2 tubulin in chemotherapy-induced peripheral neuropathy and the important role CCP1 plays in generating delta-2 tubulin.

9. EXAMPLE 4: DELTA-2-TUBULIN IS SUFFICIENT TO AFFECT MITOCHONDRIAL MOTILITY IN PERIPHERAL NEURONS

Figure 15A:
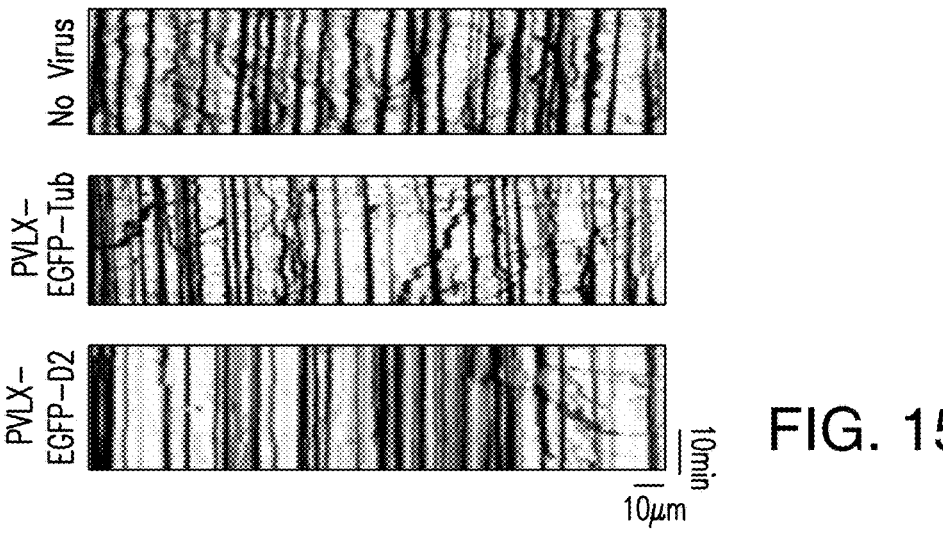
Figure 15B:
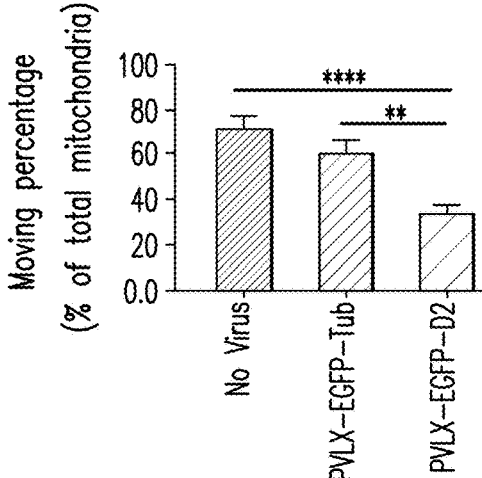
Figure 15C:
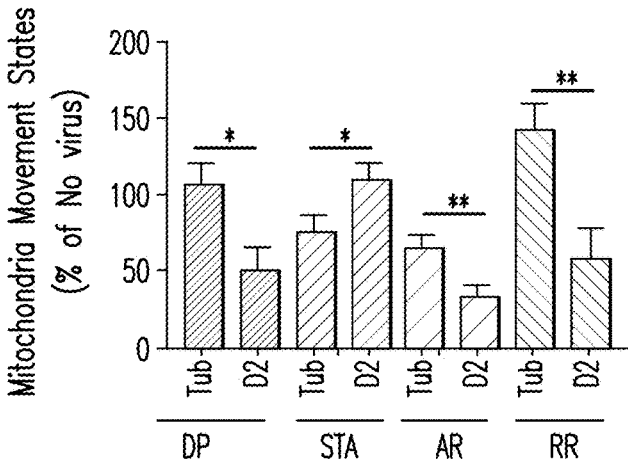

To determine the effect bortezomib and delta-2 tubulin accumulation have on mitochondrial motility, DRG neurons were transduced with lentivirus to express wild-type tubulin or delta-2 tubulin. As shown in FIGS. 15A and B, DRG neurons that expressed delta-2 tubulin showed a significant reduction in the motility of the mitochondria in the neurons as compared to control neurons or neurons that expressed wild-type tubulin. Expression of delta-2 tubulin affected every state of mitochondrial movement analyzed except for the stationary state (STA) (FIG. 15C). The effect of CCP1 knockdown on mitochondrial movement in the presence of bortezomib was also analyzed. As shown in FIG. 15D, treatment with bortezomib greatly affected the movement of mitochondria in DRG neurons. However, the knockdown of CCP1 activity rescued the effects bortezomib had on the motility of the mitochondria (FIG. 15D-F).

10. REFERENCES

Cavaletti and Marmiroli, Nature Reviews Neurology 6:657-666 (2010).

Ghosh-Roy et al., Developmental Cell 23:716-728 (2012).

Hong et al. Cuff. Oncol. 21(4):174-180 (2014).

Janke and Kneussel, Trends in Neuroscience 33:362-372 (2010).

Soucek et al., Prostate 66:954-955 (2006).

Rogowski et al., Cell 143:564-578 (2010).

UniProtKB Q9UPW5.

Various references, patents and patent applications are cited herein, the contents of which are hereby incorporated by reference in their entireties.

We claim:

1. A method for the treatment of chemotherapy-induced peripheral neuropathy in a subject having cancer, the method comprising:

determining an increased level of delta-2-tubulin in a sample of nervous tissue obtained from the subject, and administering an effective amount of an siRNA or shRNA targeting cytosolic carboxypeptidase 1 (CCP1), cytosolic carboxypeptidase 4 (CCP4), or cytosolic carboxypeptidase 6 (CCP6) or a pharmaceutical composition thereof.

2. The method of claim 1, wherein the chemotherapy is selected from the group consisting of oxaliplatin, cisplatin, carboplatin, paclitaxel, eribulin, thalidomide, a taxane, a vinca alkaloid and bortezomib.

3. The method of claim 2, wherein the chemotherapy is bortezomib.

4. The method of claim 1, wherein the siRNA targets cytosolic carboxypeptidase 1 (CCP1).

5. The method of claim 1, wherein the shRNA targets cytosolic carboxypeptidase 1 (CCP1).

6. The method of claim 1, wherein the expression level of delta-2-tubulin is determined by immunofluorescence or Western Blot.

7. The method of claim 1, wherein the sample comprises one or more peripheral neuronal cells.

8. The method of claim 1, wherein the sample is a biopsy of a peripheral nerve.

9. The method of claim 1, wherein the sample is a dermal biopsy.

* * * * *